US007585512B1

(12) United States Patent
Berd

(10) Patent No.: US 7,585,512 B1
(45) Date of Patent: *Sep. 8, 2009

(54) COMPOSITION AND METHOD OF USING TUMOR CELLS

(75) Inventor: David Berd, Wyncote, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/203,004

(22) Filed: Feb. 28, 1994

Related U.S. Application Data

(63) Continuation-in-part of application No. 07/985,334, filed on Dec. 4, 1992, now Pat. No. 5,290,551, which is a continuation of application No. 07/520,649, filed on May 8, 1990, now abandoned.

(51) Int. Cl.
 *A61K 39/00* (2006.01)
 *A61K 39/385* (2006.01)
(52) U.S. Cl. .................. 424/277.1; 424/193.1
(58) Field of Classification Search ............. 424/193.1, 424/277.1; 530/807
 See application file for complete search history.

(56) References Cited

U.S. PATENT DOCUMENTS

| 4,108,983 | A |   | 8/1978  | Wallack ................... 424/89 |
|-----------|---|---|---------|-----------------------------------|
| 4,232,001 | A | * | 11/1980 | Jensen et al. ................. 424/1 |
| 4,237,224 | A |   | 12/1980 | Cohen et al. ................ 435/68 |
| 4,683,195 | A |   | 7/1987  | Mullis et al. .................. 435/6 |
| 4,683,202 | A |   | 7/1987  | Mullis ...................... 435/91 |
| 4,800,159 | A |   | 1/1989  | Mullis et al. ............ 435/172.3 |
| 4,883,750 | A |   | 11/1989 | Whiteley et al. ............... 435/6 |
| 5,008,183 | A | * | 4/1991  | Osther ........................ 435/5 |
| 5,290,551 | A | * | 3/1994  | Berd ......................... 424/88 |
| 5,484,596 | A | * | 1/1996  | Hanna et al. ............. 424/277.1 |
| 5,626,843 | A | * | 5/1997  | Skurkovich et al. ...... 424/140.1 |
| 5,651,993 | A | * | 7/1997  | Edelson et al. ............. 424/534 |
| 5,702,704 | A | * | 12/1997 | Bucala ................... 424/137.1 |

FOREIGN PATENT DOCUMENTS

| EP | 0 329 822 A2 | 8/1988 |
| EP | 0 320 308 A2 | 12/1988 |
| GB | 2 218 420 A  | 11/1989 |
| WO | WO 87/06270  | 10/1987 |
| WO | WO 87/06840  | 11/1987 |
| WO | WO 88/10315  | 12/1988 |
| WO | WO 89/06700  | 7/1989 |
| WO | WO 89/09284  | 10/1989 |
| WO | WO 90/11764  | 10/1990 |
| WO | WO 94/21792  | 9/1994 |
| WO | WO 95/15334  | 6/1995 |

OTHER PUBLICATIONS

Stedman's Medical Dictionary, Williams & Wilkins, Baltimore, pp. 157 & 1541, 1990.*
Bystrn J.C., Cancer Metastasis Rev. 9: 81-91, 1990.*
Finn U.J., Current Opinion in Immunology S: 707-708, 1993.*
Bend et al. Proc Am Assoc Cancer Res Annu Meet 30(0): 382, 1989.*
Murphy et al. Lab Invest 62(1): 70A, 1990.*
Patt:110 R.A. Am J. Obstet. Gynocol 124(8): 808-817, 1976.*
Houver- et al Cancer 55: 1236-1243, 1985.*
Livingston, Proc Natl Acad Sci 84:2911-2915, 1987.*
Hellstrom et al Annals of the N.Y Acad Sci 640:24-33, 1993.*
Murray et al. *Harperis Biochemistry* $21^{st}$ ed, Appleton & Lang, Norwalk, CT 1988 p. 24 & 32.*
McCune et al (Cancer 43:1619-1623), 1979.*
McCune et al (Cancer 47:1984-1987), 1981.*
Sanda et al (J. Cellular Biochem. Suppl., 17, Part D, p. 120, 1993.*
Wiseman et al (Western J. Med., 151:283-288), 1989.*
Berd et al (Proc. Am. Soc. Clin. Oncol., 2:56), 1983.*
Moody et al (J. Urol., 145:293A), 1991.*
Berd et al (Cancer Research, 1986, 46:2572-2577)).*
Roitt et al (Immunology, 3rd edition, Mosby, 1993, St. Louis, p. 2.10).*
von Blomberg et al (Immunology, 1980, 39:291-299).*
Anichini A. et al. Cytotoxic T Lymphocyte Clones From Peripheral Blood and From Tumor Site Detect Intratumor Heterogeneity of Melanoma Cells *J. Immunol* 1989 142:3692.
Berd et al., Augmentation of the Human Immune Response by Cyclophosphamide *Cancer Res.* 1982 42:4862-4866.
Berd et al., Impairment of Concanavalin A-inducible Suppressor Activity following Administration of Cyclophosphamide to Patients with Advanced Cancer *Cancer Res.* 1984 44:1275-1280.
Berd et al., Induction of Cell-mediated Immunity to Autologous Melanoma Cells and Regression of Metastases after Treatment with A Melanoma Cell Vaccine Preceded by Cyclophosphamide *Cancer Res.* 1986 46:2572-2577.
Berd et al., Active Immunotherapy of Human Melanoma Exploiting the Immunopotentiating Effects of Cyclophosphamide *Cancer Invest.* 1988 6:337-349.
Berd et al., Potentiation of Human Cell-mediated and Humoral Immunity by Low-Dose Cyclophosphamide *Cancer Res.* 1984 44:5439-5443.
Berd et al., Effect of Low Dose Cyclophosphamide on the Immune System of Cancer Patients: Reduction of T-Suppressor Function without Depletion of the CD8+ Subset[1] *Cancer Res.* 1987 47:3317-3321.
Berd et al., Effect of Low Dose Cyclophosphamide on the Immune Systems of Cancer Patients: Depletion of CD4+, 2H4+ Suppressor-inducer T-Cells[1] *Cancer Res.* 1988 48:1671-1675.

(Continued)

*Primary Examiner*—Christopher H Yaen
(74) *Attorney, Agent, or Firm*—Morgan, Lewis & Bockius, LLP

(57) ABSTRACT

The present invention is directed to a treatment for cancer. Compositions and methods of treating cancer are included in the scope of the present invention. The compositions of the present invention include a composition prepared from tumor cells or tumor cell extracts. The methods of the present invention are directed to treating cancer comprising administering a therapeutically effective amount of a composition comprising tumor cells and/or tumor cell extracts.

8 Claims, 12 Drawing Sheets

OTHER PUBLICATIONS

Berd et al., An Unusual Pattern of Tumor Regression in Melanoma Patients Treated with Cyclophosphamide (CY)+ Autologous Tumor Cell Vaccine *Proc Amer. Assoc. Cancer Res.* 1988 29:408.

Berd et al., Immunization with Haptenized, Autologous Tumor Cells Induces Inflammation of Human Melanoma Metastases *Cancer Res.* 1991 51:2731.

Berendt M.J. T-Cell-Mediated Suppression of Anti-Tumor Immunity *J. Exp. Med.* 1980 151:69.

Boerrigter and Scheper Local and Systemic Desensitization Induced by Repeated Epicutaneous Hapten Application *J. Invest. Dermatol.* 1987 88:3.

Butler J.E. The Amplified ELISA: Principles of and Applications for the Comparative Quantitation of Class and Subclass Antibodies and the Distribution of Antibodies and Antgens in Biochemical Separates *Methods Enzymol.* 1981 73:482.

Bystryn J. Antibody Response and Tumor Growth in Syngeneic Mice Immunized to Partially Purified B16 Melanoma-Associated Antigens *J. Immun.* 1978 120:96.

Fearon E.R. et al Interleukin-2 Production by Tumor cells Bypasses T Helper Function in the Generation of an Antitumor Response *Cell* 1990 60:397.

Flood et al., Protective Immunity To Progressive Tumors Can Be Induced by Antigen Presented on Regressor Tumors *J. Immunol* 1987 138:3573-3579.

Fujiwara H. et al., The Augmentation of In Vitro and In Vivo Tumor-Secific T cell-Mediated Immunity by Amplifier T Lymphocytes *J. Immunol* 1980 124:863.

Fujiwara et al., Enhanced TNP-Reactive Helper T Cell Activity and its Utilization in the Induction of Amplified Tumor Immunity that Results in Tumor Regression *J. Immunol* 1984 132:1571-1577.

Fujiwara et al., Establishment of A Tumor-Specific Immunotherapy Model Utilizing TNP-Reactive Helper T Cell Activity and Its Application ot The Autochthonous Tumor System *J. Immunol.* 1984 133:510-514.

Geczy A.F. et al. Lymphocyte Transformation in Contact Sensitivity *Immunol.* 1970 19:189.

Lotze et al., Systemic Administration of Interleukin-2 in Humans *J. Biol. Response* 1982 3:475-482.

Meuer et al., Low-Dose Interleukin-2 Induces Systemic Immune Responses Against HBsAg In Immunodeficient Non-Responders to Hepatitis B Vaccination *Lancet* 1989 1:15-18.

Miller and Claman, The Induction of Hapten-Specific T Cell Tolerance by Using Hapten-Modified Lymphoid Cells *J. Immunol* 1976 117:1519-1526.

Mitchison, Immunologic Approach to Cancer *Transplant Proc.* 1970 2:92-103.

Mukherji B. et al. Regulation of Cellular Immune Response Against Autologous Human Melanoma *J. Immunol* 1986 136:1888.

Old L.J. Cancer Immunology: The Search for Specificity—G.H.A. Clowes Memorial Lecture *Cancer Res.* 1981 41:361.

Ortmann, B. et al, Synthetic Peptides Anchor T Cell-Specific TMP Eptiopes to MHC Antigens *J. Immunol.* 1992 148:1445.

Rotzschke et al. Isolation and analysis of naturally processed viral peptides as recognized by cytotoxic T cells *Nature* 1990 348:252.

Ruiter MHC antigens in human melanomas D.J. *Seminars in Cancer Bio* 1991 2:35.

Shearer F.M. Cell-mediated cytotoxicity to trinitrophenyl-modified syngeneic lymphocytes *J. Immunol* 1974 4:527.

Talmadge et al., Systematic Preclinical Study on the Therapeutic Properties of Recombinant Human Interleukin 2 for the Treatment of Metastatic Disease *Cancer Res.* 1984 47:5725-5732.

Topalian et al., Immunotherapy of Patients with Advanced cancer Using Tumor-Infiltrating Lymphocytes and Recombinant Interleukin-2: A Pilot Study *J. Clin. Oncol.* 1988 6:839-853.

Townsend S.E. Tumor Rejection After Direct Costimulation of CD8+ T Cells by B7-Transfected Melanoma Cells *Science* 1993 259:368.

Tsutsui H. et al. Drug-Specific T Cells Derived From patients with drug-Induced Allergic Hepatitis *J. Immunol* 1992 149:706.

Van derBruggen P. et al. The Encoding an Antigen Recognized by Cytolytic T Lymphocytes on a Human Melanoma *Science* 1991 254:1643.

West et al., Constant-Infusion Recombinant interleukin-2 in Adoptive Immunotherapy of Advanced Cancer *New Eng. J. Med.* 1987 316:898-903.

Wysocki and Sato "Panning" for lymphocytes: A method for cell selection *Proc. Natl. Acad. Sci. USA* 1978 75:2844.

Yamamura et al. Defining Protective Responses to pathogens: Cytokine Profiles in Leprosy Lesions *Science* 1991 254:277.

Berd et al. Treatment of Human Melanoma with a Hapten-Modified Autologous Vaccine *Annals New York Academy of Sciences* 1993 690:147-152.

Carding et al. A polymerase chain reaction assay for the detection and quantitation of cytokine gene expression in small numbers of cells *Jour. Immun. Methods* 1992 151:277-287.

Gunning et al. Isolation and Characterization of Full Length cDNA Clones for Human α-, B-, and γ-Actin mRNAs: Skeletal but Not Cytoplasmic Actins Have an Amino-Terminal Cysteine that Is Subsequently Removed. *Molec. and Cell. Bio.* 1983 787-795.

Kaashoek et al. Cytokine Production by the Bladder Carcinoma Cell Line 5637: Rapid Analysis of mRNA Expression Levels Using a cDNA-PCR Procedure *Lymphokine and Cytokine Res.* 1991 10:231-235.

Kanangat et al. Use of Quantitative Polymerase Chain Reaction to Quantitate Cytokine Messenger RNA Molecules *Molecular Immunology* 1992 29:1229-1236.

Kosugi et al. Cross-Reactivity between Haptenic Myramyl Di- or Tripeptide Derivatives and Mycobacterium bovis BCG: Potential Application for Enhancing Tumor Immunity *Infection and Immunity* 1986 54:768-773.

Luscher et al. The pattern of cytokine gene expression in freshly excised human metastatic melanoma suggests a state of reversible anergy of tumor-infiltrating lymphocytes Int. *J. Cancer* 1994 57:612-619.

MacLean et al. Active Immunization of Human Ovarian Cancer Patints Against a Common Carcinoma (Thomsen-Friedenreich) Determinant Using a Synthetic Carbohydrate Antigen *J. Immun.* 1992 11:292-305.

Nitta et al. Expression of Tumour Necrosis Factor-α, -β and Interferon-γ Genes Within Human Neuroglial Tumour Cells and Brain Specimens *Cytokine* 1994 6:171-180.

Sia et al. Studies in the enhancement of tumour immunity by coupling strong antigens to tumour cells ('heterogenization of tumours'). Helper T cell clones against PPD help other T cells mount anti-tumor responses to PPD-coupled tumour cells *Immunology* 1984 51:755-763.

Vieira et al. Isolation and expression of human cytokine synthesis inhibitory factor cDNA clones: Homology to Epstein-Barr virus open reading frame BCRFI *Proc. Natl. Acad. Sci. USA* 1991 88:1172-1176.

Pattillo, R. Immunotherapy and chemotherapy of gynecologic cancers *Am. J. Obstet. Gynecol.* 1976 124(8):808-817.

Murphy et al. Tumor Infiltrating T Cells in Metastatic Melanoma: Induction by Immunization with Autologous, DNP-Conjugated Tumor Cells Annual Meeting Abstracts *Laboratory Investigation* Rubin (ed) Proceedings of American Acad. Of Path. 1990 70 (A).

Hoover et al. Prospectively Randomized Trial of Adjuvant Active-Specific Immunotherapy for Human Colorectal Cancer *Cancer* 1985 55:1236-1243.

Livingston et al. Vaccines containing purified GM2 ganglioside elicit GM2 antibodies in melanoma patients *Proc Natl Acad Sci* 1987 84:2911-2915.

Hellstrom et al. Tumor Immunology: An Overview *Annals New York Academy of Sciences* 1993 690:24-33.

Finn O. Tumor-rejection antigens recognized by T lymphocytes *Cancer* 1993 701-708.

Bystryn J. Tumor vaccines *Cancer and Metastasis Reviews* 1990 9:81-91.

Heike, M., et al Membranes Activate Tumor- and Virus-Specific Precursor Cytotoxic T Lymphocytes In Vivo and Stimulate Tumor-Specific T. Lymphocytes in Vitro: Implications for Vaccination *J. Immunotherapy* 1994 15:165-174.

Slingluff, C., et al Recognition of Human Melanoma Cells by HLA-A2. 1-Restricted Cytotoxic T Lymphocytes Is Mediated by at Least Six Shared Peptide Epitopes *J Immunology* 1993 150:2955-2963.

Wolfel et al. Isolation of Naturally Processed Peptides Recognized by Cytolytic T Lymphocytes (CTL) on Human Melanoma Cells in Association with HLA-A2.1 *Int. J. Cancer* 1994 57:413-418.

Mossman et al. Two Types of Murine Helper T Cell Clone *J. Immunol.* 1986 136:2348.

Scott et al. Role of Cytokines and CD4+ T-Cell Subsets in the Regulation of Parasite Immunity and Disease *Immunoligcal Review* 1989 112:161-182.

Scott IFN-γ Modulates the Early Development of Th1 and Th2 Responses in a Murine Model of Cutaneous Leishmaniasis *J. Immunol.* 1991 147:3149-3155.

Fiorentino et al IL-10 Acts on The Antigen-Presenting Cell to Inhibit Cytokine Production by Th1 Cells *J. Immunol.* 1991 146:3444-3451.

Pisa et al Selective expression of interleukin 10, interferon γ, and granulocyte-macrophage colony-stimulating factor in ovarian cancer biopsies *Proc. Natl. Acad. Sci. USA* 1992 89:7708-7712.

Gastl et al. Interleukin-10 Production by Human Carcinoma Cell Lines and Its Relationship to Interleukin-6 Expression *Int. J. Cancer* 1991 55:96-101.

Chen, et al Production of IL-10 By Melanoma Cells: Examination of its Role in Immunosuppression Mediated By Melanoma *Int. J. Cancer* 1994 56:755-760.

Livingston et al. Phase 1 trial immunological adjuvant QS-21 with a GM2 ganglioside-keyhole limpet haemocyanin conjugate vaccine in patients with malignant melanoma *Vaccine* 1991 12:1275.

Lee et al. Changes in expression of DC45R during the development of $T_h1$ and $T_h2$ cell lines *Eur. J. Immunol.* 1992 22:1455-1459.

Jinquan et al. Human IL-10 is a Chemoattractant for CD8+ T Lymphocytes and an Inhibitor of IKL-8-Induced CD4+ T Lymphocyte Migration *J. Immunol.* 1993 151:4545-4551.

Walker et al. Isothermal in vitro amplification of DNA by a restriction enzyme/DNA polymerase system *Proc. Natl. Acad, Sci. (U.S.A.)* 1992 89:392-396.

Kwoh et al. Transcription-based amplifcation system and detection of amplified human immunodeficiency virus type 1 with a bead-based sandwich hybridization format *Proc. Natl. Acad. Sci. (U.S.A.)* 1989 86:1173.

Ohara et al. One-sided Polymerase chain reaction: The amplificationo f cDNA *Proc. Natl. Acad. Sci. (U.S.A.)* 1989 86:5673-5677.

Wu et al. The Ligation Amplification Reaction (LAR) -Amplification of Specific DNA Sequences Using Sequential Rounds of Template-Dependent Ligation *Genomics* 1989 4:560.

Lattime et al. Limiting Dilution Analysis of TNF Producing Cells in C3H/HeJ Mice *J. Immunol.* 1988 144:3422-3428.

Bagasra et al. Polymerase chain reaction in situ: intracellular amplification and detection of HIV-1 proviral DNA and other specific genes *J. Immunol. Meth.* 1993 158:131-145.

Cardi et al. Depletion of T-Cells with the CD4+CD45R+ Phenotype in Lymphoclytes that Infiltrate Subcutaneous Metastatses of Human Melanoma *Cancer Res.* 1989 49:6562-6565.

Naylor et al. Investigation of Cytokine Gene Expression in Human Colorectal Cancer *Cancer Res.* 1990 50:4436-4440.

Lattime et al. Tumor Growth in Vivo Selects for Resistance to tumor Necrosis Factor *J. Immunol.* 1989 143:4317-4323.

O'Doherty et al. Dendritic Cells Freshly Isolated from Human Blood Express CD4 and Mature into Typical Immunostimulatory Dendritic Cells after Culture in Monocyte-conditioned Medium *J. Exp. Med.* 1993 178:1067-1078.

Nahas et al. The Ability of Hapten-Conjugated Cells to induce Cell-Mediated Cytotoxicity is Affected by the Mode of Hapten Linkage *Cellular Immunology* 1980 54:241-247.

Saito, S., et al. *Cancer Res.* 1994 54: 3516-3520.

Von Bonin, A., et al., *Int. Immunol.* 1992 4:869-874.

Hewitt et al., *Br. J. Cancer* 1976 33:241-259.

Srivastava et al., *Proc. Natl. Acad. Sci.* 1986 83:3407.

Berd et al, *J. Clin. Oncol.*, 1990 8:1858.

Lafreniere and Rosenberg, *J. Immunol.* 1985 135:4273.

Parkinson, D. R., et al,. *J. Clin. Oncol.* 1990 8:1650-1656.

Rosenberg et al., *Science* 1986 233:1318.

Bukowski et al., *Cancer Res.* 1991 51:4199.

Kempkes et al., *J. Immunol.* 1991 147:2467.

Jang et al., *Eur. J. Immunol.* 1991 21:1303.

Nalefski and Rao, *J. Immunol.* 1993 150:3806.

Helling et al., *Cancer Res.*, 1995 55:2783.

McCune et al., *Cancer* 1979 43:1619.

Bursuker et al., *Int. J. Cancer* 1991 49:414.

Pistoor et al., *J. Invest. Dermatol.* 1995 105:92.

Noguchi et al., *Proc. Natl. Acad. Sci. USA* 1995 92: 2219-2223.

Hock et al, *Cancer Res.* 1993 53: 714-716.

Berd, *Pharmacol Therap A* 1977 2:373-395.

Morton, D.L., et al., Malignant Melanoma J.F. Holland, E.I. Frei, R.C.J. Bast, D.W. Kufe, D.L. Morton and R.R. Weichselbaum (eds.), *Cancer Medicine*, pp. 1793-1824, Philadelphia: Lea and Febiger. 1993.

McCune et al., *Cancer* 1981 47: 1984-1987.

Schulof, R.S., et al., *Mol. Biother.* 1988 1:29-36.

Kantor et al., *JNCI* 1992 84:1084-1091.

Kwak et al., *N. Engl. J. Med.* 1992 327:1209-1215.

Schlag et al., *Cancer Immunol. Immunother.* 1992 35:325-330.

Simons, J.W., *Proc. Am. Assoc. Cancer Res.* 1993 35.

MacLean et al., *Cancer Immunol. Immunother.* 1993 36:215-222.

Hengst, J.C.D., et al., *Cancer Res.* 1980 40:2135-2141.

Porgador, A., et al., *Cancer Res.* 1992 52:3679-3686.

Berendt, M.J. and North, R.J., *J. Exp. Med.* 1980 151:69-80.

Shrayer, D., et al., *Cancer Immunol. Immunother.* 1995 40:277-282.

Traversari, C., et al. *J. Exp. Med.* 1992 176:1453-1457.

Brasseur, F., et al., *Int. J. Cancer* 1992 52:839-841.

Russo, V., et al., *Int. J. Cancer* 1995 64:216-22.

Weynants, P., et al., *Int. J. Cancer* 1994 56:826-829.

Russo, V., et al., *Int. J. Cancer* 1996 67:457-460.

Inou, H., et al. *Gastroenterology* 1995 109:1522-1525.

Rimoldi, D., et al., *Int. J. Cancer* 1993 54:527-528.

O'Mara, S. M., et al., *Eur. J. Cancer* 1992 28:9-11.

Filmus, J. E. and R. N. Buck, *Cancer Res.* 1985 45:4468-4472.

Lundy, J. R., et al., *J. Clin. Oncol.* 1986 4:1321-1325.

Qin, H., et al., *Cancer Res.* 1995 55:2984-2987.

Colvin, M. Alkylating Agents and Platinum Antitumor Compounds. In: J.F. Holland et al. (Eds.) Cancer Medicine Chapter IXVI, Chemotherapeutic Agents, pp. 743-749 Philadephia, Lea Febiger 1993.

Myers, C. Anthracyclines and DNA intercalators. In: J.F. Holland et al. (Eds) Cancer Medicine Chapter XVI-5 pp. 746-773, Philadelphia Lea and Febiger 1993.

* cited by examiner

COMPOSITION AND METHOD OF USING TUMOR CELLS

REFERENCE TO RELATED APPLICATIONS

This application is a continuation-in-part of application Ser. No. 07/985,334, filed Dec. 4, 1992, now U.S. Pat. No. 5,290,551, which is a continuation of application Ser. No. 07/520,649, filed May 8, 1990, now abandoned.

INTRODUCTION

The invention described herein was made in the course of work under a grant or award from an NIH Cancer Research grant, grant no. CA39248. The United States Government may have certain rights in this invention. Some of this invention was disclosed in a Disclosure Document filed with the U.S. Patent and Trademark Office on Apr. 18, 1990.

BACKGROUND OF THE INVENTION

It was theorized in the 1960's that tumor cells bear specific antigens (TSA) which are not present on normal cells and that the immune response to these antigens might enable an individual to reject a tumor. It was later suggested that the immune response to TSA could be increased by introducing new immunological determinants on cells. Mitchison, *Transplant. Proc.*, 1970, 2, 92. Such a "helper determinant", which can be a hapten, a protein, a viral coat antigen, a transplantation antigen, or a xenogenous cell antigen, could be introduced into a population of tumor cells. The cells would then be injected into an individual who would be expected to be tolerant to the growth of unmodified tumor cells. Clinically, the hope was that an immunologic reaction would occur against the helper determinants, as a consequence of which the reaction to the accompanying TSA is increased, and tumor cells which would otherwise be tolerated are destroyed. Mitchison, supra, also suggests several modes of action of the helper determinants including 1) that the unmodified cells are merely attenuated, in the sense that their growth rate is slowed down or their susceptibility to immunologic attack increased; 2) that helper determinants merely provide points of attack and so enable the modified cells to be killed by an immune response not directed against TSA; 3) that the helper determinants have an adjuvant action such as binding to an antibody or promoting localization of the cells in the right part of the body for immunization, in particular, in lymph nodes.

Fujiwara et al., *J. Immunol.*, 1984a, 132, 1571 showed that tumor cells conjugated with the hapten, trinitrophenyl (TNP), could induce systemic immunity against unmodified tumor cells in a murine system, provided that the mice were first sensitized to the hapten in the absence of hapten-specific suppressor T cells. Spleen cells from the treated mice completely and specifically prevented the growth of tumors in untreated recipient animals. Flood et al., *J. Immunol.*, 1987, 138, 3573 showed that mice immunized with a TNP-conjugated, ultraviolet light-induced "regressor" tumor were able to reject a TNP-conjugated "progressor" tumor that was otherwise non-immunologic. Moreover, these mice were subsequently resistant to challenge with unconjugated "progressor" tumor. In another experimental system, Fujiwara et al., *J. Immunol.*, 1984b, 133, 510 demonstrated that mice sensitized to trinitrochlorobenzene (TNCB) after cyclophosphamide pretreatment could be cured of large (10 mm) tumors by in situ haptenization of tumor cells; subsequently, these animals were specifically resistant to challenge with unconjugated tumor cells.

The existence of T cells which cross-react with unmodified tissues has recently been demonstrated. Weltzien and coworkers have shown that class I MHC-restricted T cell clones generated from mice immunized with TNP-modified syngeneic lymphocytes respond to MHC-associated, TNP-modified "self" peptides. Ortmann, B., et al., *J. Immunol.*, 1992, 148, 1445. In addition, it has been established that immunization of mice with TNP-modified lymphocytes results in the development of splenic T cells that exhibit secondary proliferative and cytotoxic responses to TNP-modified cells in vitro. Shearer, G. M. *Eur. J. Immunol.*, 1974, 4, 527. The potential of lymphocytes elicited by immunization with DNP- or TNP-modified autologous cells to respond to unmodified autologous cells is of considerable interest because it may be relevant to two clinical problems: I) drug-induced autoimmune disease, and 2) cancer immunotherapy. In regard to the former, it has been suggested that ingested drugs act as haptens, which combine with normal tissue protein forming immunogenic complexes that are recognized by T cells. Tsutsui, H., et al., *J. Immunol.*, 1992, 149, 706. Subsequently, autoimmune disease, e.g., systemic lupus erythematosus, can develop and continue even after withdrawal of absence of the offending drug. This would imply the eventual generation of T lymphocytes that cross-react with unmodified tissues.

The common denominator of these experiments is sensitization with hapten in a milieu in which suppressor cells are not induced. Spleen cells from cyclophosphamide pretreated, TNCB-sensitized mice exhibited radioresistant "amplified helper function" i.e., they specifically augmented the in vitro generation of anti-TNP cytotoxicity. Moreover, once these amplified helpers had been activated by in vitro exposure to TNP-conjugated autologous lymphocytes, they were able to augment cytotoxicity to unrelated antigens as well, including tumor antigens (Fujiwara et al., 1984b). Flood et al., (1987), supra, showed that this amplified helper activity was mediated by T cells with the phenotype $Lyt^-1^+$, $Lyt^-2^-$, $L3T4^+$, $I^-J^+$ and suggests that these cells were contrasuppressor cells, a new class of immunoregulatory T cell.

Immunotherapy of patients with melanoma has shown that administration of cyclophosphamide, at high dose (1000 $mg/M^2$) or low dose (300 mg/M), three days before sensitization with the primary antigen keyhole limpet hemocyanin markedly augments the acquisition of delayed type hypersensitivity to that antigen (Berd et al., *Cancer Res.*, 1982, 42, 4862; *Cancer Res.*, 1984a, 44, 1275). Low dose cyclophosphamide pretreatment allows patients with metastatic melanoma to develop delayed type hypersensitivity to autologous melanoma cells in response to injection with autologous melanoma vaccine (Berd et al., *Cancer Res.*, 1986, 46, 2572). The combination of low dose cyclophosphamide and vaccine can produce clinically important regression of metastatic tumor (Berd et al. (1986), supra; *Cancer Invest.*, 1988a, 6, 335). Cyclophosphamide administration results in reduction of peripheral blood lymphocyte non-specific T suppressor function (Berd et al., *Cancer Res.*, 1984b, 44, 5439; Cancer Res., 1987, 47, 3317), possibly by depleting CD4+, CD45R+ suppressor inducer T cells (Berd et al., *Cancer Res.*, 1988b, 48, 1671). The anti-tumor effects of this immunotherapy regimen appear to be limited by the excessively long interval between the initiation of vaccine administration and the development of delayed type hypersensitivity to the tumor cells (Berd et al., *Proc. Amer. Assoc. Cancer Res.*, 1988c, 29, 408 (#1626)). Therefore, there remains a need to increase the therapeutic efficiency of such a vaccine to make it more immunogenic.

Most tumor immunologists now agree that T lymphocyte, white cells responsible for tumor immunity, infiltration into the tumor mass is a prerequisite for tumor destruction by the immune system. Consequently, a good deal of attention has been focused on what has become known as "TIL" therapy, as pioneered by Dr. Stephen Rosenberg at NCI. Dr. Rosenberg and others have extracted from human cancer metastases the few T lymphocytes that are naturally present and greatly expanded their numbers by culturing them in vitro with Interleukin 2 (IL2), a growth factor for T lymphocytes. Topalian et al., *J. Clin. Oncol.,* 1988, 6, 839. However this therapy has not been very effective because the injected T cells are limited in their ability to "home" to the tumor cite.

The ability of high concentrations of IL2 to induce lymphocytes to become non-specifically cytotoxic killer cells has been exploited therapeutically in a number of studies (Lotze et al., *J. Biol. Response,* 1982, 3, 475; West et al., *New Engl. J. Med.,* 1987, 316, 898). However, this approach has been limited by the severe toxicity of high dose intravenous IL2. Less attention has been given to the observation that much lower concentrations of IL2 can act as an immunological adjuvant by inducing the expansion of antigen activated T cells (Talmadge et al., *Cancer Res.,* 1987, 47, 5725; Meuer et al., *Lancet,* 1989, 1, 15). Therefore, there remains a need to understand and attempt to exploit the use of IL2 as an immunological adjuvant.

Human melanomas are believed to express unique surface antigens recognizable by T lymphocytes. Old, L. J., *Cancer Res.,* 1981, 41, 361; Van der Bruggen, P., et al., *Science,* 1991, 254, 1643; Mukherji, B., et al., *J. Immunol.,* 1986, 136, 1888; and Anichini, A., et al., *J. Immunol.,* 1989, 142, 3692. However, immunotherapeutic approaches to date have been limited by the difficulty of inducing an effective T cell-mediated response to such antigens in vivo.

There are several models proposed to explicate what appears to be tolerance to human tumor-associated antigens. They include:

1) Tumor antigen-specific suppressor cells that down-regulated incipient anti-tumor responses. Mukherji, et al., supra; Berendt, M. J. and R. J. North., *J. Exp. Med.,* 1980, 151, 69.

2) Failure of human tumor cells to elicit T helper cells or to provide costimulatory signals to those T cells. Fearon, E. R., et al., *Cell,* 1990, 60, 397; Townsend, S. E. and J. P. Allison, *Science,* 1993, 259, 368; and 3) Reduced surface expression of major histocompatibility products on tumor cells which limits their recognition by T cells. Ruiter, D. J., *Seminars in Cancer Biology,* 1991, 2, 35. None of these hypotheses has yet been corroborated in a clinical system.

SUMMARY OF THE INVENTION

The present invention is directed to a treatment for cancer. Compositions and methods of treating cancer are included in the scope of the present invention. The compositions of the present invention include a composition prepared from tumor cells or tumor cell extracts. The methods of the present invention are directed to treating cancer comprising administering a therapeutically effective amount of a composition comprising tumor cells or tumor cell extracts.

BRIEF DESCRIPTION OF THE DRAWINGS

FIG. 11 shows graphs of cytotoxicity of DNP-reactive T cells. Melanoma cells, either autologous (autol) or allogeneic class I-mismatched (allo), were used as targets in a 6-hour $^{51}$Cr assay. Effector cells were expanded CD8+, DNP-reactive T cells.

DETAILED DESCRIPTION OF THE INVENTION

Figure 1:
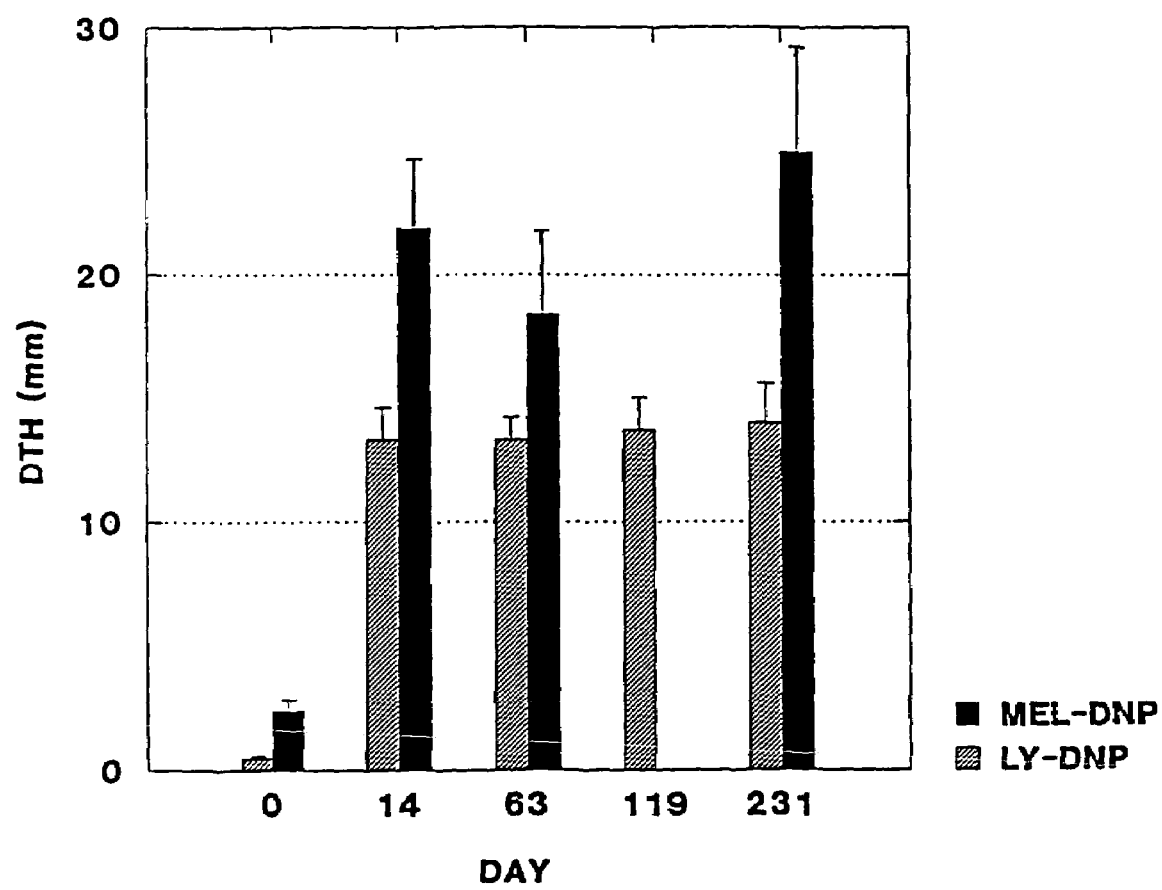
FIG. 1 displays the kinetics of the development of DTH to DNP-modified autologous PBL and melanoma cells. Patients with metastatic melanoma treated with DNP-vaccine were serially skin tested with DNP-modified PBL (LY) or DNP-modified melanoma cells dissociated from a metastatic mass (MEL). Each bar indicates the mean DTH response for the group of patients at each time point; error bars=standard error. For day 119, only responses to PBL were measured. Sample sizes: days 0, 14, 63 N=84; day 119, N=57; day 175, N=42; day 231, N=35.

The present invention is directed to cancer immunotherapy. A novel tumor composition and methods of treating cancer are included in the scope of the invention.

The present invention is directed for use in treating cancer, including metastatic and primary cancers. Cancers treatable with the present invention include the following non-limiting examples: melanoma, breast, lung, colon, breast, kidney, and prostate. Mammals, particularly humans, having metastatic cancer may be treated with the compositions and methods of the present invention.

The compositions of the present invention are prepared from tumor cells or tumor chemical extracts. The tumor cells and extracts preferably originate from the type of cancer which is to be treated. The tumor cells and extracts may be, and are not limited to, autologous and allogenic cells dissociated from biopsy specimens or tissue culture, as well as stem cells and extracts from these sources. Preferably, the cells and extracts are autologous. Extracts of the present invention comprise a peptide isolated from cancerous cells. Peptides will preferably be low molecular weight, about 9 to about 20 amino acids. Chemical or cellular extracts may be isolated from the cell surface. The extract may be particular to cancer cells (versus normal cells). Cancer specific extracts include and are not limited to peptides binding to the major histocompatibility complex, other cell surface-associated proteins, proteins encoded by cancer oncogenes or mutated anti-oncogenes. These are known to those of skill in the art. Preferably, the extract comprises chemicals unique, or substantially specific to, a particular type of cancer.

The tumor cells of the present invention may be live cells. The tumor cells and extracts of the present invention may be irradiated prior to use. Tumor cells or extracts are irradiated at 2500 cGy to prevent the cells from growing after injection.

The compositions of the invention may be employed in the method of the invention singly or in combination with other compounds, including and not limited to other compositions of the invention. Accordingly, tumor cells and tumor cell extracts may be used alone or co-administered. For purposes of the present invention, co-administration includes administration together and consecutively. Further, the tumor cells and/or extracts may be co-administered with other compounds including and not limited to cytokines such as interleukin-2, interleukin-4, gamma interferon, interleukin-12, GM-CSF. The tumor cells and extracts of the invention may also be used in conjunction with other cancer treatments including and not limited to chemotherapy, radiation, antibodies, and antisense oligonucleotides.

The compositions of the invention may be administered in a mixture with a pharmaceutically-acceptable carrier, selected with regard to the intended route of administration and the standard pharmaceutical practice. Dosages may be set with regard to weight, and clinical condition of the patient. The proportional ratio of active ingredient to carrier naturally depend on the chemical nature, solubility, and stability of the compositions, as well as the dosage contemplated. Amounts of the tumor cells and extracts of the invention to be used depend on such factors as the affinity of the compound for cancerous cells, the amount of cancerous cells present and the solubility of the composition. The compounds of the present invention may be administered by any suitable route, including inoculation and injection, for example, intradermal, intravenous, intraperitoneal, intramuscular, and subcutaneous.

The compositions of the present invention may be administered alone or will generally be administered in admixture with a pharmaceutical carrier selected with regard to the intended route of administration and standard pharmaceutical practice.

The composition of the present invention is a therapeutically effective amount of an irradiated composition selected from the group consisting of live tumor cells, tumor cell extracts, and a mixture of tumor cells and tumor cell extracts. The composition may be mixed with an immunological adjuvant and/or a pharmaceutically acceptable carrier.

In a preferred embodiment of the invention, the composition comprises a vaccine consisting of about $10 \times 10^6$ to about $25 \times 10^6$, more preferably about $5 \times 10^6$ to about $25 \times 10^6$, live, irradiated, tumor cells suspended in a pharmaceutically acceptable carrier or diluent, such as and not limited to Hanks solution, saline, phosphate-buffered saline, and water, to which is added an immunological adjuvant, such as and not limited to, Bacillus Calmette-Guerin (BCG). The tumor cells and extracts may be conjugated to a hapten. The mixture is injected intradermally into 3 contiguous sites per administration on the upper arms or legs, excluding limbs ipsilateral to a lymph node dissection.

Patients may be immunized to the chemical dinitrophenyl (DNP) by application of dinitrofluorobenzene (DNFB) to the skin. Two weeks later, the patients are injected with a vaccine, irradiated and haptenized to DNP. The vaccine is reinjected every 4 weeks for a total of eight treatments. The drug, cyclophosphamide (CY) is administered 3 days prior to each vaccine administration to augment the immune response to the tumor cells. A non-haptenized form of the vaccine may be similarly administered.

The vaccine of the present invention may be haptenized or non-haptenized. The haptenized, or chemically-linked, form of the vaccine may include a tumor cell haptenized to dinitrophenyl (DNP) for example. Other haptens include and are not limited to trinitrophenyl (TNP) and N-iodoacetyl-N'-(5-sulfonic 1-naphtyl)ethylene diamine (AED). A vaccine of tumor cell extracts may similarly be haptenized. The present invention also contemplates a non-haptenized vaccine of tumor cells and/or cell extracts.

In the methods of the present invention, a method of treating a patient suspected of having cancer, comprises administering a pharmaceutically acceptable amount of cyclophosphamide, a pharmaceutically acceptable amount of a composition selected from the group consisting of live tumor cells, tumor cell extracts, and a mixture of tumor cells and tumor cell extracts. The composition may be mixed with an immunological adjuvant and/or a pharmaceutically acceptable carrier. The haptenized vaccine may optionally be followed by administration of a pharmaceutically acceptable amount of a non-haptenized vaccine. A non-haptenized vaccine may also be administered in accordance with the methods of the present invention.

The vaccine of the present invention may comprise tumor cells and/or tumor cell extracts. The tumor cells for use in the present invention may be prepared as follows. Tumor masses are processed as described by Berd et al. (1986), supra, incorporated herein by reference in its entirety. The cells are extracted by enzymatic dissociation with collagenase and DNAse by mechanical dissociation, frozen in a controlled rate freezer, and stored in liquid nitrogen until needed. On the day that a patient is to be skin tested or treated, the cells are thawed, washed, and irradiated to 2500 R. They are washed again and then suspended in Hanks balanced salt solution without phenol red. Conjugation of the prepared cells with DNP is performed by the method of Miller and Claman, *J. Immunol.*, 1976, 117, 1519, incorporated herein by reference in its entirety, which involves a 30 minute incubation of tumor cells with DNFB under sterile conditions, followed by washing with sterile saline.

Chemical extracts of the cancer cells are prepared by protein extraction techniques from the cancer cells, followed by antigen assays to determine the most effective antigen(s) for patient treatment. The methods of isolating cell extracts are readily known to those skilled in the art. Briefly, cancerous cells are isolated from a tumor and cultured in vitro. Dinitrophenyl is added to the cultured cells. Peptides are isolated from cells according to an established technique of Rotzschke et al., *Nature*, 1990, 348, 252, the disclosure of which is hereby incorporated by reference in its entirety. The cells are treated with a weak acid. Then they are centrifuged and the supernatants are saved. Fractions containing small peptides are obtained by HPLC, concentrated, and frozen. The fractions are screened for immunological activity by allowing them to bind to autologous B lymphoblastoid cells which are then tested for ability to stimulate melanoma-specific T lymphocytes.

Human cancer vaccines have been developed and tested by a number of workers. Although they can sometimes induce weak immunity to a patient's cancer, they rarely cause tumor regression. The development of inflammatory responses in metastatic tumors was surprisingly found with the DNP-vaccine of the present invention. The tumor becomes reddened, warm and tender. Ultimately, in some cases, the tumor regresses to the extent that the tumor disappears, to the naked eye and microscopically. Microscopically, infiltration of T lymphocytes into the tumor mass is observed. Therefore, this approach, which increases the inflammatory response and the number and capacity of lymphocytes entering the tumor, is a significant advance in the art.

The effectiveness of the vaccine may be improved by adding various biological response modifiers. These agents work by directly or indirectly stimulating the immune response. Biological response modifiers of the present invention include and are not limited to interleukin-12 and gamma interferon. In this embodiment, IL12 will be given following the each vaccine injection. Administration of IL12 to patients with inflammatory responses causes the T lymphocytes within the tumor mass to proliferate and become more active. The increased T cell numbers and functional capacity leads to immunological destruction of the tumors. Dosages for IL12 will be prepared in accordance with the dosage indications set forth above.

Patients with metastatic melanoma were treated using an immunotherapy regimen with the following components: 1) vaccine consisting of autologous tumor cells conjugated to DNP; and 2) low dose cyclophosphamide pretreatment. Patients were evaluated to determine whether tumor regression had occurred, to monitor tumor inflammatory responses, and to measure delayed type hypersensitivity to autologous melanoma cells, DNFB (the form of DNP used for skin sensitization), DNP-conjugated autologous lymphocytes, diluent (Hanks solution), purified protein derivative (PPD), and recall antigens (candida, trichophyton, and mumps). Patients who are considered to be deriving benefit (clinical or immunological) from the therapy are continued in the immunotherapy regimen. Subsequent vaccines may be given without cyclophosphamide. In a similar experiment, Interleukin 2 linked to polyethylene glycol was found to not be effective.

In another embodiment, a vaccine comprising chemical extracts of cancer cells conjugated to a hapten and mixed with an immunological adjuvant, such as Bacillus Calmette-Guerin, BCG, is used.

The invention is further illustrated by means of the following examples which are meant to be illustrations only and are not intended to limit the present invention to these specific embodiments.

Example 1

Sixty-four patients were treated with metastatic melanoma using a melanoma vaccine, prepared in accordance with the methods set forth above, preceded by low dose cyclophosphamide (CY) and monitored for immunological effects and anti-tumor activity. On day 0, the patients were given cyclophosphamide 300 mg/$M^2$ i.v. Three days later, they were injected intradermally with vaccine consisting of $10 \times 10^6$ to $25 \times 10^6$ autologous, cryopreserved, irradiated (2500 R) tumor cells mixed with BCG; the tumor cells were obtained by dissociation of metastatic masses enzymatically (collagenase and DNAse). This treatment sequence was repeated every 28 days for 8 treatments.

The toxicity of the therapy was limited to a local inflammatory response at the injection site and mild nausea and vomiting following cyclophosphamide administration. There were 40 evaluable patients with measurable metastases; 5 had responses—4 complete and 1 partial. The median duration of response was 10 months (7-84+months). One patient continues to be in remission at 11 years. Regression occurred not only in skin and nodal metastases, but also in lung and liver metastases. In 6 additional patients, an anti-tumor response was observed that seemed peculiar to this vaccine therapy, i.e., the regression of metastatic lesions that appeared after the immunotherapy was begun. In 3 patients this "delayed" regression occurred in two or more tumors.

Delayed-type hypersensitivity (DTH) to autologous, mechanically-dissociated melanoma cells was detectable in only 16% of patients before treatment, as compared with in 46%, 56% and 73% of patients on days 49, 161 and 217, respectively. The increases in delayed type hypersensitivity following immunotherapy were statistically significant by a non-independent t-test: day 0 vs. day 49, $p<0.001$; day 0 vs. day 161, $p<0.001$; day 0 vs. day 217, $p=0.021$. Overall, 26/43 patients (61%) exhibited a positive delayed type hypersensitivity response ($\geq 5$ mm) to autologous melanoma cells at some time point. Patients also developed strong delayed type hypersensitivity to the enzymes used to prepare the tumor cell suspensions: of 24 patients tested for delayed type hypersensitivity with a mixture of collagenase and DNase (each at 1 µg/ml) after two vaccine treatments, 21 (88%) had responses >5 mm. Anti-tumor responses to the vaccine were strongly associated with delayed type hypersensitivity to mechanically-dissociated, autologous melanoma cells, as indicated by three observations: 1) 8/10 patients who exhibited tumor regression had positive delayed type hypersensitivity; 2) in post-surgical adjuvant patients, there was a highly significant correlation between the intensity of delayed type hypersensitivity to autologous melanoma cells and the time to recurrence of tumor (r=0.680, p<0.001); 3) nine patients who developed delayed type hypersensitivity to the autologous melanoma cells in their original vaccine ("old" tumor) developed new metastases ("new" tumor) that did not elicit delayed type hypersensitivity or elicited a much smaller response. The patients were compared to their condition prior to treatment with the vaccine. The patients treated prior to the vaccine study were removed from treatment one to two months prior to starting the vaccine study. Accordingly, the patients were untreated beginning the vaccine study.

In three cases we were able to excise regressing tumors for histological examination; such tumors were characterized by an intense infiltration of lymphocytes. In contrast, tumors excised from these patients before immunotherapy consisted of homogeneous masses of malignant cells without significant lymphocytic infiltration.

This study shows that the use of cyclophosphamide allows the development of an immune response to melanoma-associated antigens in cancer-bearing patients.

Example 2

Patients with metastatic melanoma were sensitized to DNP by topical application to the upper arm with 1% dinitrochlorobenzene (DNCB) or dinitrofluorobenzene (DNFB). Two weeks later they were injected with a vaccine consisting of $10 \times 10^6$ to $25 \times 10^6$ autologous, irradiated melanoma cells conjugated to DNP and mixed with BCG. Cyclophosphamide 300 mg/M² i.v. was given 3 days before DNCB (or DNFB) or vaccine. Of 4 evaluable patients, 3 have developed a striking inflammatory response in tumor masses after 2 vaccine treatments (8 weeks). Patient #1 developed erythema and swelling in the >50 large (1-3 cm) dermal metastases on her leg and lower abdomen, followed by ulceration and drainage of necrotic material, and some are beginning to regress. Biopsy showed infiltration with CD4+ CD8+ T lymphocytes. Patient #2 developed erythema and swelling in the skin of her lower abdomen and groin overlying large (8 cm) nodal masses. These have not yet regressed, but have changed in consistency from rockhard to fluctuant. Patient #3 exhibited moderate erythema in the skin overlying 3 subcutaneous metastases. All 3 patients have developed delayed type hypersensitivity to both DNCB and to DNP conjugated autologous lymphocytes. The patients were compared to their condition prior to treatment with the vaccine. The patients treated prior to the vaccine study were removed from treatment one to two months prior to starting the vaccine study. Accordingly, the patients were untreated beginning the vaccine study.

Example 3

Fifteen patients (including 3 patients from Example 2) were treated with metastatic-melanoma using a novel form of immunotherapy, i.e., tumor cell vaccine conjugated to DNP. Patients were sensitized to DNP by topical application to the upper arm with 5% dinitrochlorobenzene. Then every 4 weeks they received cyclophosphamide 300 mg/M² followed 3 days later by injection of $10 \times 10^6$ to $25 \times 10^6$ autologous, irradiated melanoma cells conjugated to DNP. Patients received 6-8 treatments. Most patients (92%) developed delayed-type hypersensitivity (DTH) to DNP-conjugated autologous lymphocytes or tumor cells (mean DTH=17 mm). The vaccine induced a striking inflammatory response in subcutaneous and nodal metastases in 11/15 patients, consisting of erythema, swelling, warmth, and tenderness around tumor masses, and, in one case, purulent drainage. Biopsies showed infiltration with lymphocytes, which, by immunopathological and flow cytometric analyses, were mainly CD3+, CD4−, CD8+, HLA-DR+ T cells. The melanoma cells in these tissues strongly expressed ICAM-1, which serves as an adhesion molecule for T cells. Thus, DNP-vaccine seems to induce a degree of anti-melanoma immunity not seen with previously tested immunotherapy. The patients were compared to their condition prior to treatment with the vaccine. The patients treated prior to the vaccine study were removed from treatment one to two months prior to starting the vaccine study. Accordingly, the patients were untreated beginning the vaccine study.

Example 4

This example examined the therapeutic effects of DNP-vaccine in patients with surgically-resected metastases and no clinical evidence of metastatic disease. Forty seven patients were sensitized to the hapten, DNFB (dinitrofluorobenzene). Then they were treated by intradermal injection of autologous, irradiated melanoma cells conjugated to DNP. Additional vaccine injections were administered ever 28 days for a total of eight treatments. All patients were periodically tested for Delayed Type Hypersensitivity, DTH, responses to autologous melanoma cells, DNP-conjugated autologous lymphocytes, and microbial antigens. In vitro studies were performed with cryopreserved lymphocytes extracted from metastatic tumors and/or separated from peripheral blood.

| | DNP-VACCINE THERAPY OF MELANOMA | | | | | | | | | | | | |
|---|---|---|---|---|---|---|---|---|---|---|---|---|---|
| | DAY OF WEEK | | | | | | | | | | | | |
| | M | W | F | M | T | M | W | TH | M | TH | M | W | M |
| DAY OF STUDY | −21 | −19 | −17 | −14 | −13 | 0 | 2 | 3 | 28 | 31 | 49 | 51 | 56 |
| CYCLOPHOSPHAMIDE | | X | | | | X | | | X | | | | REPEAT |
| DNP VACCINE | | | | | | | | X | | X | | | CYCLE |
| DNFB SENS | | | | X | X | | | | | | | | FOR |
| DNFB CHALL | | | | | | X | | | | | | | A |
| APPLY SKIN TESTS | X | | | | | X* | | | | | X | | TOTAL |

-continued

| DNP-VACCINE THERAPY OF MELANOMA | | | | | | | | | | | | |
|---|---|---|---|---|---|---|---|---|---|---|---|---|
| | DAY OF WEEK | | | | | | | | | | | |
| | M | W | F | M | T | M | W | TH | M | TH | M | W | M |
| READ SKIN TESTS | | X | | | | | | X | | | | X | OF |
| OBTAIN PBL | X | | | | | X | | | | | X | | 8 |
| OBTAIN SERUM | X | | | | | X | | | | | X | | VACCINE |
| ROUTINE LABS | X | | | | | | | | | | X | | |

CY (cyclophosphamide) = 300 mg/M$^2$ i.v. bolus only before first two vaccines
VACCINE = 5 × 10$^6$ to 20 × 10$^6$ autologous, irradiated melanoma cells mixed with BCG
DNFB SENS = 1.0 mg in 0.1 ml acetone-corn-oil applied to ventral upper arm
DNFB CHALL = 200 μg in 0.1 ml acetone-corn-oil applied to forearm
APPLY SKIN TESTS = autologous melanoma cells, peripheral blood lymphocytes (PBL), peripheral blood lymphocytes conjugated to DNP (PBL-DNP), purified protein derivative (PPD) (skin test for tuberculosis), microbial recall antigens
*Day 0: PBL, PBL-DNP only
READ SKIN TESTS = mean diameter of induration
OBTAIN PBL = 100 cc heparinized blood
ROUTINE LABS = complete blood count (CBC), differential blood count (diff), platelet count (platelets), SMA-12 (panel of routine lab tests, blood urea nitrogen (BUN)

Sensitization to DNP—Patients initially were sensitized to DNP as follows: On day −17, cyclophosphamide, 300 mg/M$^2$, was administered as a rapid i.v. infusion. Three days later, on days −14 and −15, patients were sensitized with DNFB (dinitrofluorobenzene): 1 mg DNFB dissolved in acetone-corn oil and applied topically in a volume of 0.1 ml within the confines of a 2 cm diameter steel ring. Two weeks later, patients were tested for reactivity to DNP by topical application of 200 μg DNFB and intradermal injection of DNP-conjugated autologous PBL. Cyclophosphamide was reconstituted in sterile water and the proper dosage was administered by rapid i.v. infusion.

Vaccine Preparation—Tumor masses were processed. Cells were extracted by enzymatic dissociation with collagenase and DNAse and by mechanical dissociation, frozen in a controlled rate freezer, and stored in liquid nitrogen until needed. On the day that a patient was to be treated, the cells were thawed, washed, and irradiated to 2500 R. Then they were washed again and suspended in Hanks balanced salt solution without phenol red.

Conjugation of melanoma cells with DNP was performed. This involved a 30 minute incubation of tumor cells with dinitrofluorobenzene (DNFB) under sterile conditions, followed by washing with sterile saline.

The vaccine consists of 5–20×10$^6$ live tumor cells suspended in 0.2 ml Hanks solution. When BCG is added, it consisted of 0.1 ml of a 1:10 dilution of Tice BCG. Each vaccine treatment consisted of three injections into contiguous sites on the upper arms or legs, excluding limbs ipsilateral to a lymph node dissection.

Study Procedure—On day 0, patients received cyclophosphamide 300 mg/M$^2$ as a rapid i.v. infusion. Three days later, on day +3, they were injected intradermally with autologous melanoma vaccine. Additional vaccine injections were administered every four weeks for a total of eight treatments. Cyclophosphamide was given only prior to the first two injections. All vaccines were DNP-conjugated and mixed with Bacillus Calmette-Guerin (BCG). BCG is the Tice strain (substrain of the Pasteur Institute strain) obtained from Organon Teknika Corporation, Durham, N.C. The freeze-dried material was reconstituted with 1 ml sterile water and diluted 1:10 in phosphate-buffered saline, pH 7.2; then 0.1 ml was drawn up, mixed with the vaccine and injected. All vaccines were injected into the same site (upper arm or leg).

Immunological evaluation—Skin-testing was performed by the intradermal injection of 0.1 ml of test material on the forearm, and delayed type hypersensitivity was assessed at 48 hours by measuring the mean diameter of induration. Positive reactions were photographed. The following materials were tested: 1) 1×10$^6$ irradiated autologous melanoma cells; 2) 3×10$^6$ autologous peripheral blood lymphocytes, both unconjugated and conjugated to DNP; 3) Hanks solution; 4) PPD-intermediate strength; and 5) microbial recall antigens—Candida, trichophyton, and mumps. Also, contact sensitivity to DNFB was tested by applying 200 μg to the skin of the forearm and examining the area for a circle of induration at 48 hours.

All patients had blood collected for separation and cryopreservation of lymphocytes and serum each time skin-testing was performed (see Table 1 for schedule of blood drawing). Periodically, these were tested for: 1) proliferative and cytotoxic response to autologous melanoma cells; and 2) proliferative response to DNP-conjugated autologous lymphocytes.

Duration of Study

1) Patients were treated with eight courses of vaccine which required about eight months. Treatment was then stopped. These patients will be monitored until at least five years has elapsed since their initial surgery.

2) Patients who developed regional recurrence or distant metastases before the completion of eight treatments were taken off the study and treated as clinically indicated (chemotherapy or surgery).

The control group consisted of 22 patients with melanoma metastatic to regional lymph nodes. They underwent surgical resection of their disease, at which time they had no clinical evidence of metastatic melanoma. Then, they received treatment with a non-haptenized, autologous melanoma vaccine. First, they were given cyclophosphamide, 300 mg/M$^2$ Three days later they were injected intradermally with the vaccine, which consisted of 10×10$^6$ to 25×10$^6$ irradiated, autologous melanoma cells mixed with BCG. The cyclophosphamide-vaccine treatment was repeated every 28 days. A total of eight treatments was given. The patients were clinically evaluated every two months.

Only 20% of the control patients were cancer-free at two years. In contrast, patients treated with the DNP-vaccine of the invention had significantly higher cancer-free survival as set forth above.

The patients who received haptenized vaccine all had melanoma metastatic to regional lymph nodes, but no evidence of distant metastases. Patients in this condition are routinely treated by surgical resection of the diseased nodes. Surgical resection renders them clinically disease-free, but they have an 80-85% chance of developing metastatic melanoma with two years.

The patients in the control group were in the same clinical condition in order to be comparable to the haptenized vaccine group. Thus, the control group also consisted of patients with melanoma metastatic to regional lymph nodes, but no evidence of distant metastases, who had undergone surgical resection of the diseased nodes. When treatment was initiated with the non-haptenized vaccine, the control patients were clinically disease-free, but as previously noted, 80% developed distant metastases.

Patients with surgically incurable melanoma were not selected as controls because such patients have a cure rate approaching zero, and an even shorter survival than patients with resectable lymph node metastases. Moreover, it is not possible in such patients to measure disease-free survival, a parameter that was dramatically prolonged by the vaccine of the present invention.

A statistical analysis of the data was performed as follows: Kaplan-Meir plots of disease-free survival and total survival were constructed. The difference between DNP-vaccine patients and control patients was analyzed by the Mantel log-rank test. These are standard statistical methods for analyzing such data. The difference was highly significant with $p<0.01$.

Seventeen patients additional were subsequently treated according to the protocol outlined above (the size of the control group was not increased for reasons set forth above). The results maintained statistically significant differences in disease-free survival and total survival.

Example 5

Administration of an autologous, dinitrophenyl (DNP)-conjugated melanoma vaccine induces T cell infiltration of metastatic tumors, and prolongs survival of patients who have undergone lymphadenectomy for bulky regional metastases. These effects appear to be due to melanoma-specific T cells. Their generation is contingent upon T cells with specificity for DNP-modified melanoma cells (DNP-MEL).

Clinical Protocol

All patients had metastatic melanoma and were undergoing immunotherapy with autologous, DNP-conjugated tumor vaccine, as previously described in Berd, D., et al., *Cancer Res.*, 1991, 51, 273 I, incorporated herein by reference in its entirety. Informed consent was obtained from the patients. Patients were pre-treated with cyclophosphamide 300 mg/M$^2$, see Berd et al. (1986) supra, and three days later were sensitized to DNFB by topical application of 0.1 ml of a 1 DNFB solution in acetone-corn oil on two consecutive days. Two weeks later patients were again given cyclophosphamide, followed 3 days later by injection of DNP-conjugated melanoma vaccine. DNP-vaccine was repeated every 28 days. Cyclophosphamide was given prior to the first two cycles. The vaccine consisted of $10\times10^6$-$25\times10^6$ cryopreserved, autologous, irradiated (2500 R), DNP-conjugated melanoma cells conjugated to DNP mixed with BCG. All tumor preparations contained lymphocytes which were the residua of tumor-infiltrated lymph node tissue. Serum and PBL were collected at the following time points: day 0 (before sensitization), day 14 (2 weeks after DNFB sensitization), day 63 (after 2 vaccines), day 119 (after 4 vaccines), day 175 (after 6 vaccines), and day 231 (after 8 vaccines).

Cellular Reagents

PBL were separated by density gradient centrifugation on Ficoll metrizoate. They were suspended in freezing medium (RPMI-1640 (Mediatech, Washington D.C.)+1% human albumin+10 dimethyl sulfoxide) frozen in a controlled-rate freezer, and stored in liquid nitrogen. HLA typing of PBL was performed by the Thomas Jefferson University Hospital Clinical Laboratory.

Melanoma cells were enzymatically extracted from metastatic masses according to the method of Berd, D., et al., (1986) supra, incorporated herein by reference in its entirety, and cryopreserved. Cell lines were derived from these suspensions and were maintained in RPMI-1640 with 10% fetal calf serum. Melanoma cell lines from the patients used in this study were distinguished by MHC class I differences determined by flow cytometric analysis with a panel of monoclonal antibodies obtained from the American Type Culture Collection: (HB82=HLA-A2, HB122=HLA-A3, HB164=HLA-A11,24).

Hapten Conjugation

PBL were DNP-modified by a 30 minute incubation with aqueous DNFB or DNBS, according to the methods of Miller, S. D. and H. N. Claman, *J. Immunol.*, 1976, 117, 1519 and Geczy, A. F. and A. Baumgarten, *Immunology*, 1970, 19, 189, (incorporated herein by reference in their entirety) respectively; the two methods yielded equivalent results. For specificity controls, cells were modified with TNP by incubation with TNBS, or with oxazolone, according to the methods of Fujiwara, H., et al., *J. Immunol.*, 1980, 124, 863 and Boerrigter, G. H. and R. J. Scheper, *J. Invest. Dermatol.*, 1987, 88, 3, (incorporated herein by reference in their entirety) respectively. Hapten conjugation was repeated with melanoma cells.

Delayed-Type Hypersensitivity (DTH)

Cryopreserved PBL were thawed, washed, and resuspended in Hanks balanced salt solution. The cells were divided into three groups: unmodified, conjugated to DNP, and conjugated to TNP. After washing, $1\times10^6$ melanoma cells or $3\times10^6$ PBL were suspended in 0.1 ml Hanks solution and injected intradermally on the forearm. DTH was determined at 48 hours by measuring the mean diameter of induration. The DTH assay was repeated with melanoma cells.

All patients developed DTH to DNP-modified autologous PBL (FIG. 1). DTH responses were evident two weeks after topical application of DNFB (day 14), and then remained stable throughout the period of monthly vaccine administration. DNP-conjugated autologous melanoma cell suspensions elicited stronger DTH than DNP-PBL (mean SE: PBL=13.3 mm±1.3 mm, melanoma cells=21.9 mm±3.6 mm; p<0.01). DTH was specific for DNP-modified "self", since autologous PBL conjugated to TNP elicited no response in 50 patients tested.

Anti-DNP Antibody

An ELISA was developed by coating microtiter wells with DNP-conjugated PBL. This method was found to be preferable to coating plates with DNP-conjugated albumin because it resulted in lower background readings with serum of pre-immunized patients. DNP-conjugated PBL ($5\times10^5$ in 0.1 ml) were added to each well of 96 flat bottom plate. The cells were fixed to the plate by drying followed by a 5 minute exposure to 100% methanol. Then, the plates were washed five times with phosphate buffered saline +0.05% Tween-20. Serial dilutions of test sera were added to the wells and the plate was incubated in a humidified chamber at 37° C. for 1 hour. After the incubation, the plate was washed five times, and then horse radish peroxidase-conjugated goat anti-human immunoglobulin (Cappel Laboratories, Malvern, Pa.) was added at predetermined optimal dilution. For detecting IgG or IgM antibodies, peroxidase-conjugated goat anti-human IgG or IgM were used, respectively. After a 1 hour incubation at 37° C., the plate was washed five times and 0.1 ml of substrate (O-phenylenediamine, Sigma Chemical Co., St. Louis, Mo.) was added to each well followed by 50 µl of 0.12% hydrogen peroxide. The plate was read in an ELISA plate reader.

The assay was validated using a murine anti-DNP monoclonal antibody (clone SPE-7; Sigma ImmunoChemicals) and a peroxidase-conjugated antimouse immunoglobulin antibody as the second step reagent. Subsequently, the positive control consisted of a serum sample from a patient who had received multiple injections of DNP-vaccine. Anti-DNP antibody titer of each serum sample was defined as follows: (peak OD of sample) X (reciprocal of the dilution having an OD equal to half the peak OD of positive control) Butler, J. E., *Methods Enzymol.*, 1981, 73, 482.

Figure 2:
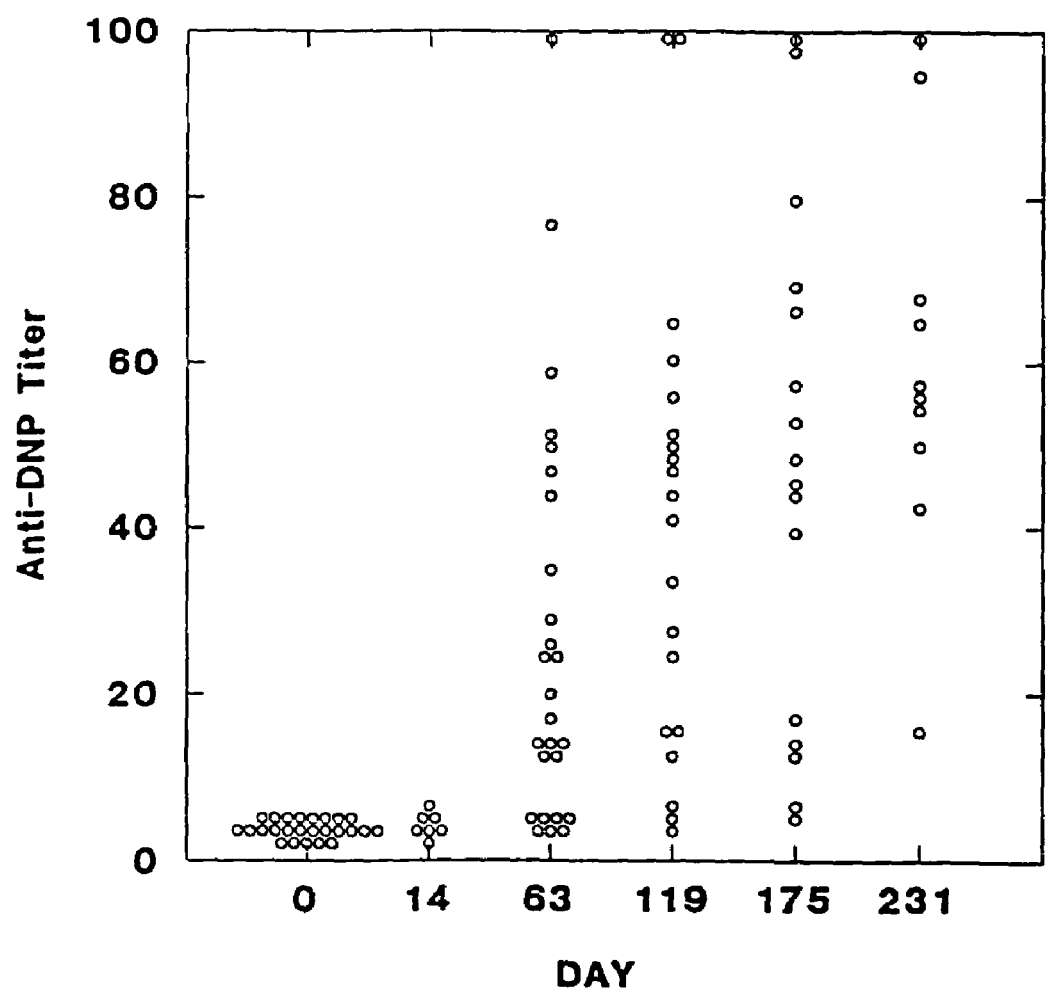
FIG. 2 exhibits antibody response to DNP. Serum obtained at various time points was tested for antibody (total immunoglobulin) to DNP using an ELISA. The titer was defined as: (peak OD of sample)×(reciprocal of the dilution that gave an OD equal to half the peak OD of positive control).

Anti-DNP antibody developed in 24 out of 27 patients tested (FIG. 2). In contrast to DTH, antibody was not induced by DNFB topical application (day 14). In 19 patients, titers increased above pre-immunization levels after two intradermal injections of DNP-conjugated melanoma cells (day 63); in 5 additional patients, significant titers were found only after 4 to 6 vaccines. In all patients, IgG antibody was detected; anti-DNP IgM was found in only three patients. Anti-DNP antibody cross reacted with TNP, shown by binding to TNP-modified cells, but not to the unrelated hapten, oxazolone.

Development of T Cell Lines

PBL ($1 \times 10^6$) were mixed with autologous DNP-conjugated B lymphoblastoid cells ($1 \times 10^5$) in 24 well flat bottom plates in lymphocyte culture medium. After 7 days of culture, IL2 100 U/ml (a gift of Cetus Oncology, Emeryville, Calif.) was added. Expanding T cell cultures were maintained in medium +IL2 and were split as needed to maintain a concentration of about $2 \times 10^6$ cells in a 22 mm diameter well. Every 14 days, the cultures were restimulated by adding autologous DNP-conjugated B lymphoblastoid cells.

Phenotypes were determined by flow cytometry with a panel of monoclonal antibodies (Becton-Dickinson, San Jose, Calif.). Separation of CD8+ and CD4+ T cells was accomplished by indirect panning in which T cells coated with anti-CD8 or anti-CD4 monoclonal antibodies were adhered to anti-immunoglobulin-coated dishes using standard techniques according to the methods of Wysocki, L. J. and V. L. Sato, *Proc. Natl. Acad. Sci. USA*, 1978, 75, 2844, incorporated herein by reference in its entirety; the adherent cells were isolated and expanded with DNP-modified stimulators and IL2.

Phenotypically homogeneous subpopulations of T cells were obtained by culturing at limiting dilution in round-bottom microtiter wells in lymphocyte culture medium containing $2 \times 10^5$ irradiated allogeneic feeder cells, 200 U/ml IL2, and phytohemagglutinin. Wells with growing lymphocyte colonies were screened for ability to proliferate in response to DNP-modified B lymphoblastoid cells. Positive wells were expanded in IL2 and restimulated with autologous DNP-conjugated B lymphoblastoid cells every 14 days.

Lymphoproliferative Responses —PBL were tested as responder cells. They were suspended in lymphocyte culture medium (RPMI-1640, 10% pooled human AB+ serum, insulin-transferrin-selenite media supplement (Sigma Chemical Co.) 2 mM L-glutamine, 1% non-essential amino acids, 25 mM HEPES buffer, penicillin +streptomycin) and added to 96-well, round bottom microtiter plates at $1 \times 10^5$ cells/well. Stimulator cells included: 1) autologous or allogeneic PBL, 2) autologous or allogeneic B lymphoblastoid lines made by transfection with Epstein-Barr virus, 3) autologous cultured melanoma cells; they were inactivated by irradiation (5000 R). In most experiments, the responder:stimulator ratio was 1:1. The plates were incubated in a $CO_2$ incubator at 37° C. for 5 days; then the wells were pulsed with $^{125}$I-labeled IUDR (ICN Radiochemical, Costa Mesa, Calif.) for 6 hours, harvested with an automatic harvesting device, and counted in a gamma counter. The mean of triplicate wells was calculated. Cultured T cells were also tested for a lymphoproliferative response in accordance with the above methods.

Figure 3:
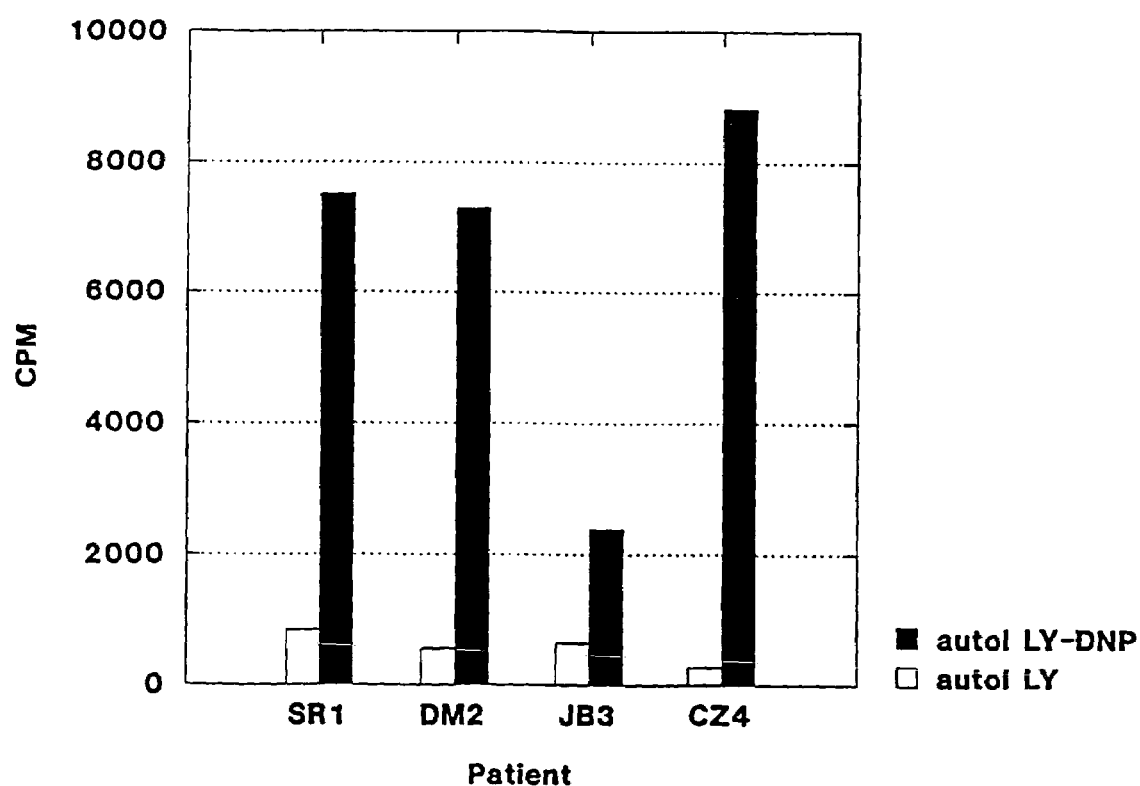
FIG. 3 is a graph of proliferative response of PBL to DNP-modified autologous lymphocytes. PBL were obtained from four patients receiving DNP-vaccine at the peak of their DTH responses. The cells were tested for ability to proliferate to DNP modified autologous PBL (autol LY-DNP) with unmodified autologous PBL (autol LY) as a control. Cultures were pulsed with $^{125}$IUDR on day 6.
Figure 4:
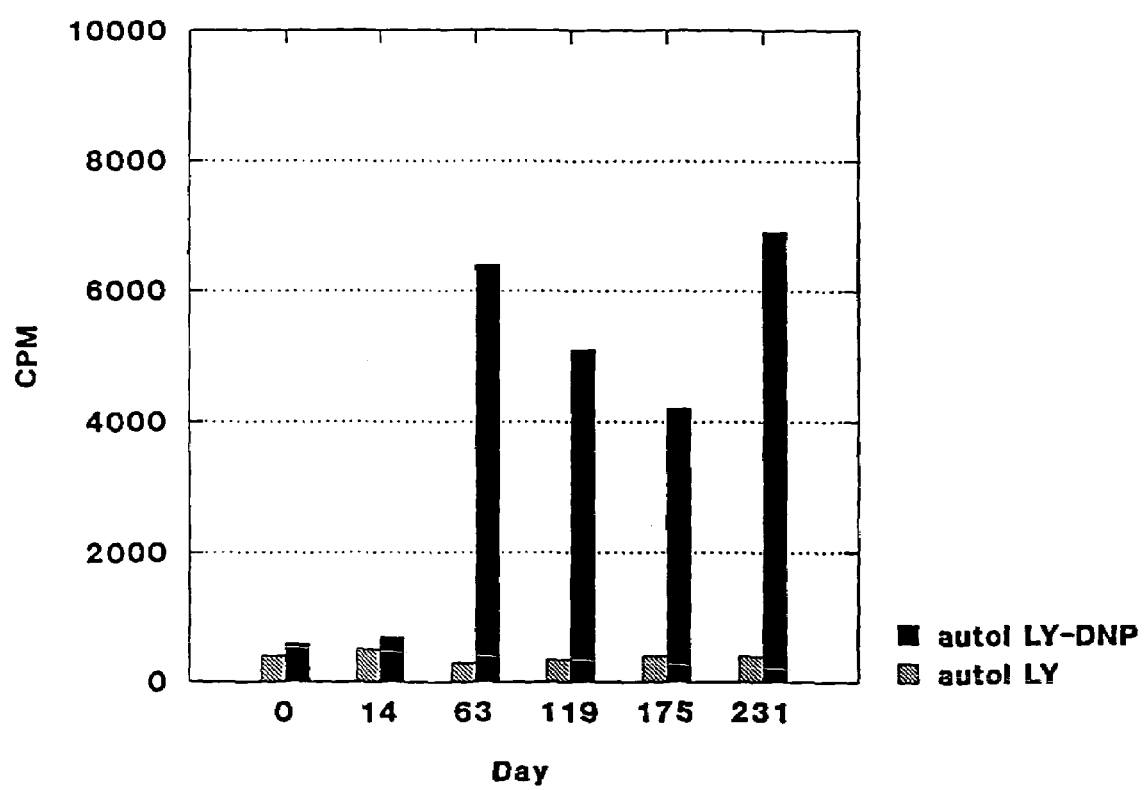
FIG. 4 shows the kinetics of the proliferative response to DNP-modified lymphocytes. PBL were serially collected from patient DM2 while receiving DNP vaccine. They were cryopreserved and then all samples were tested simultaneously for proliferative response to DNP-modified autologous PBL (autol LY-DNP). Cultures were pulsed with $^{125}$IUDR on day 6.

PBL, obtained and cryopreserved from four patients at the time of maximum DTH reactivity to DNP-modified autologous cells, were thawed and tested for in vitro proliferative responses. PBL from all four patients proliferated upon stimulation with DNP-modified cells (FIG. 3). The kinetics of the development of the proliferative response in one of these patients (DM2) is shown in FIG. 4. DNFB application alone (day 14) did not result in detectable numbers of circulating responding cells. Reactive PBL were detected after two injections of DNP-vaccine (day 63) and continued to be detected throughout the 8 months period of vaccine treatment.

Figure 5:
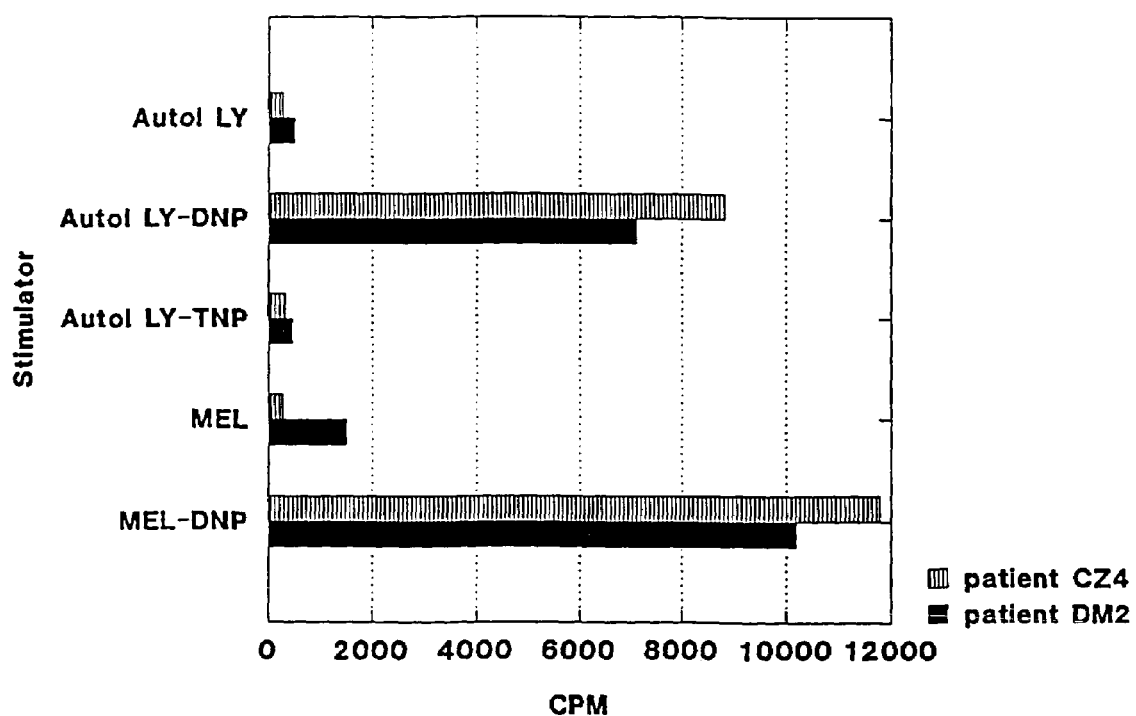
FIG. 5 displays specificity of the proliferative response to DNP-modified cells. PBL from two patients were tested for proliferative response to autologous PBL, either unmodified (autol LY), DNP-modified (autol LY-DNP), or TNP-modified (autol LY-TNP), and to cultured autologous melanoma cells, either unmodified (MEL) or DNP-modified (MEL-DNP). Cultures were pulsed with $^{125}$IUDR on day 6.

The proliferative response to DNP-modified cells was specific, since neither unconjugated PBL nor PBL modified with TNP evoked responses (FIG. 5). Post-vaccine PBL also proliferated briskly when stimulated with a DNP-modified melanoma cell line derived from autologous tumor tissue. When stimulated with allogeneic lymphocytes, PBL exhibited the expected mixed lymphocyte reaction which was three to five-fold greater than the DNP responses.

Figure 6:
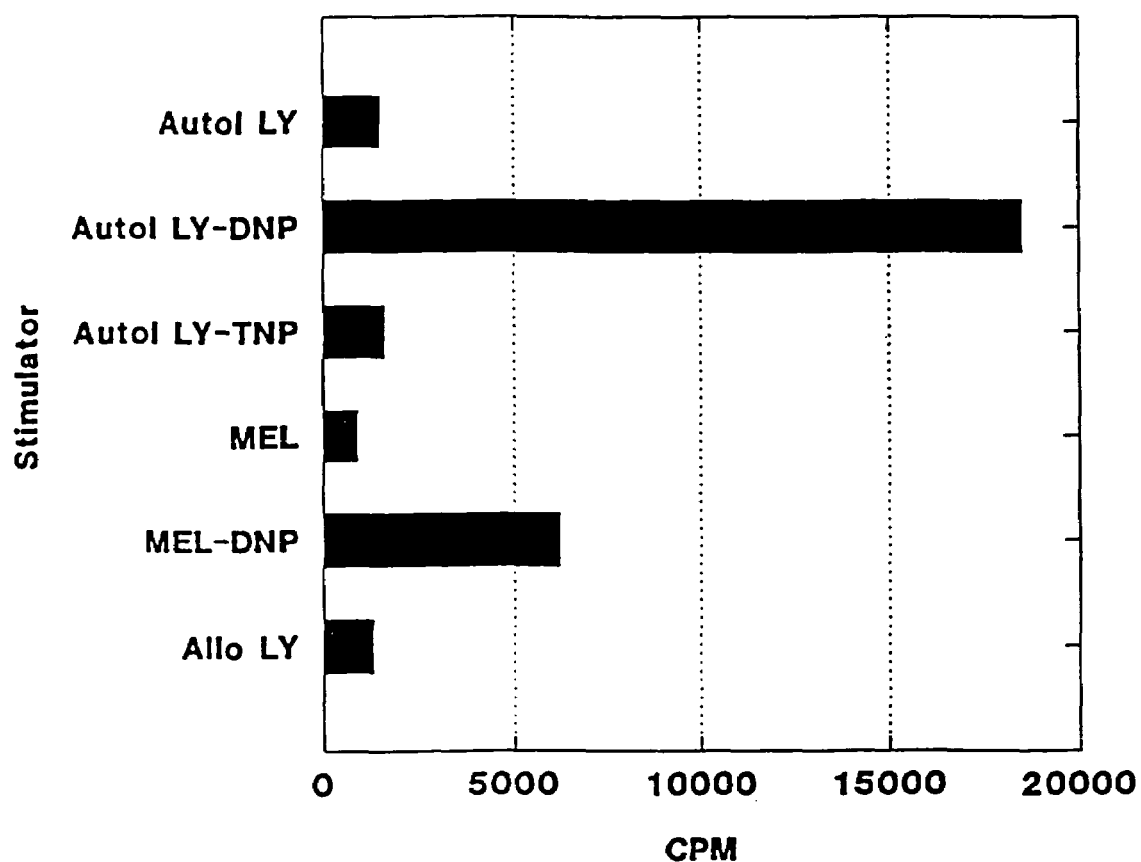
FIG. 6 is a specificity analysis of expanded T cells. PBL from patient DM2 were expanded in IL2 and repeatedly stimulated with autologous DNP-modified B lymphoblastoid cells. They were tested for proliferative response to autologous PBL, either unmodified (autol LY), DNPmodified (autol LY-DNP), or TNP-modified (autol LY-TNP); cultured autologous melanoma cells, either unmodified (MEL) or DNP-modified (MELDNP); and allogeneic PBL (Allo LY). Cultures were pulsed with 125IUDR on day 6.
Figure 7:
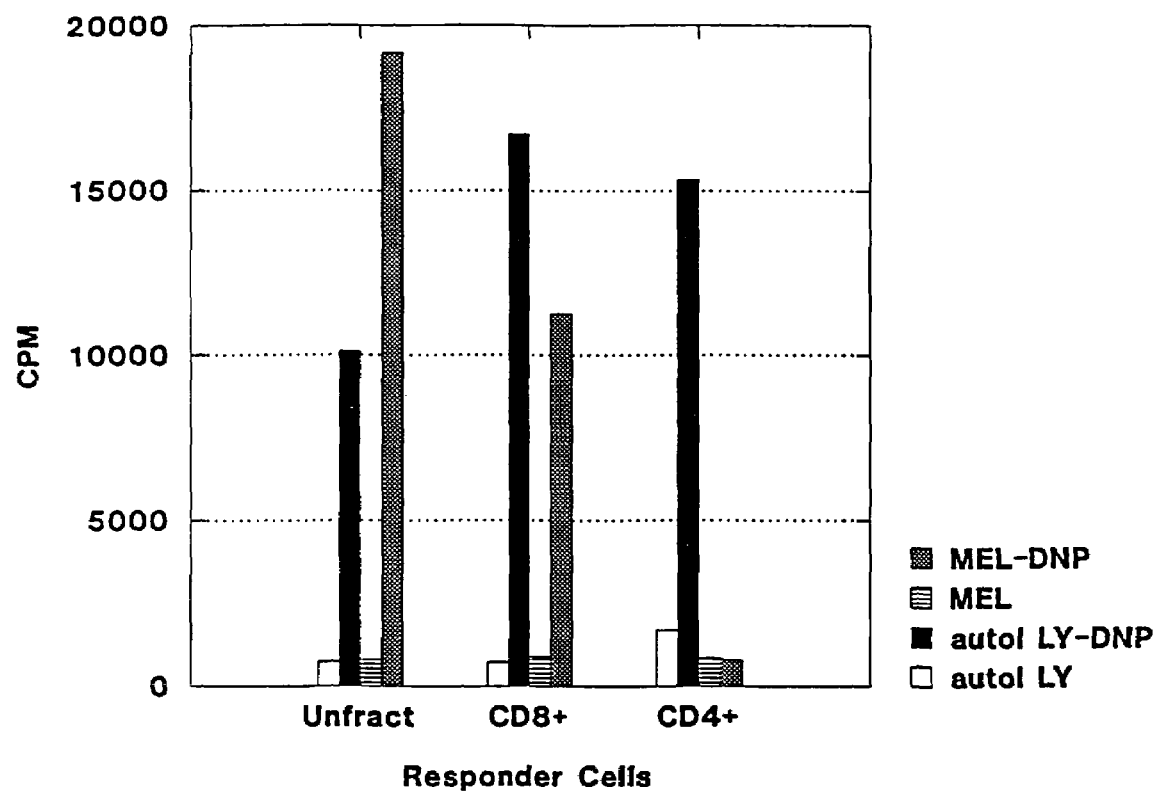
FIG. 7 displays responses of CD8+ and CD4+ T cells to DNP-modified autologous cells. Expanded T cells were separated into CD8-enriched or CD4-enriched populations by positive panning. Then they were tested for proliferative response to autologous PBL, either unmodified (autol LY), DNP-modified (autol LY-DNP), and to cultured autologous melanoma cells, either unmodified (MEL) or DNP-modified (MEL-DNP). Cultures were pulsed with $^{125}$IUDR on day 6.

Circulating T lymphocytes from one of these patients (DM2) were expanded in vitro by culture in IL2 and repeated restimulation with autologous DNP-modified B lymphoblastoid cells. After four weeks of expansion, the T cells were 70% CD3+, CD8+ and 30% CD3+, CD4+. They proliferated when stimulated by autologous, DNP-modified B lymphoblastoid cells or DNP-modified, cultured melanoma cells, but not by unconjugated autologous cells (FIG. 6). These cells were separated by positive panning into CD8-enriched and CD4-enriched populations that were 98% pure as determined by flow cytometry analysis. As shown in FIG. 7, both CD4-enriched and CD8-enriched T cells exhibited a proliferative response to DNP-modified autologous B lymphoblastoid cells. However, only CD8+ T cells responded to DNP-modified autologous melanoma cells. This result may have been due to the low constitutive expression (<5%) of MHC class II by the melanoma cell line.

Figure 8:
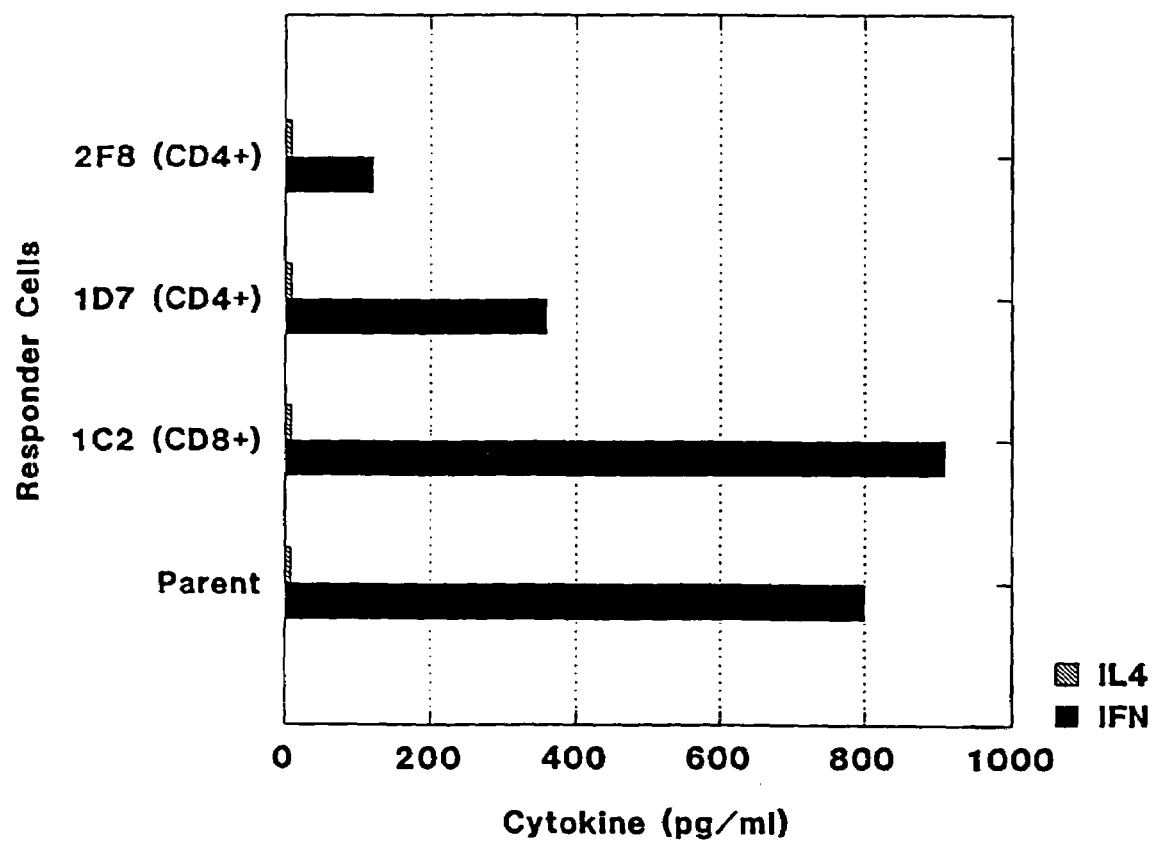
FIG. 8 shows cytokine production by DNP-reactive T cells. The DNP-reactive T cell line ("Parent"), and three subcultures (2F8, 1D7, 1C2), obtained by plating at limiting dilution, were incubated with autologous DNP-modified B lymphoblastoid cells for 18 hours; supernatants were collected and assayed for gamma interferon (IFN) and IL4.

Expanded T cells were tested for ability to produce cytokines when stimulated with autologous, DNP-modified B lymphoblastoid cells. As shown in FIG. 8, they produced gamma interferon but not IL4. To determine whether both CD4+ and CD8+ T cells were involved in the cytokine response, sublines that were obtained by plating T cells at limiting dilution were analyzed. Each of these cultures was homogeneous in respect to expression of CD4 and CD8. Three of these sublines (two CD4+, one CD8+) were tested for cytokine response to DNP-modified B lymphoblastoid cells. All three produced gamma interferon, while none made IL4 (FIG. 8).

Cytokine Production—T cells were added to round bottom microtiter plates at $1\times10^5$ cells/well. An equal number of stimulators (DNP-modified autologous B lymphoblastoid cells) was added, and supernatants were collected after 18 hours incubation. Commercially available ELISA kits were used to measure gamma interferon (Endogen, Boston, Mass.; sensitivity 5 pg/ml) and IL4 (R&D Systems, Minneapolis, Minn.; sensitivity=3 pg/ml).

To determine the MHC-dependence of the response, stimulator cells were pre-incubated with monoclonal antibodies to MHC class I (W6/32) or MHC class II (L243) at a concentration of 10 μg/ml for one hour before adding responder cells. Non-specific mouse immunoglobulin at the same concentration was tested as a negative control.

Figure 9:
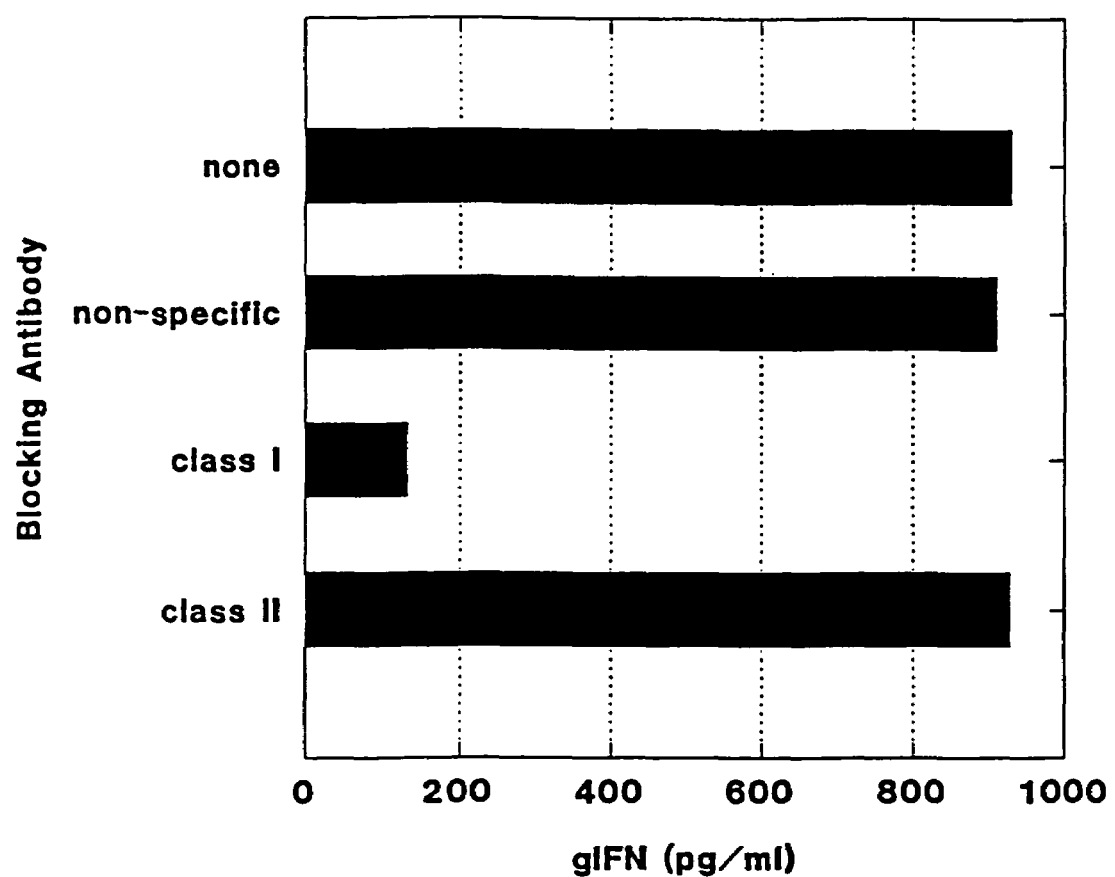
FIG. 9 shows blocking of T cell response by anti-MHC class I monoclonal antibody. Expanded CD8+ T cells were stimulated with autologous DNP-modified B lymphoblastoid cells and the cultures were assayed for gamma interferon after 18 hours. Stimulator cells were pre-incubated with one of the following: no antibody (none), non-specific mouse IgG (non-specific), monoclonal antibody W6/32 (class I), or monoclonal antibody L243 (class II).
Figure 10:
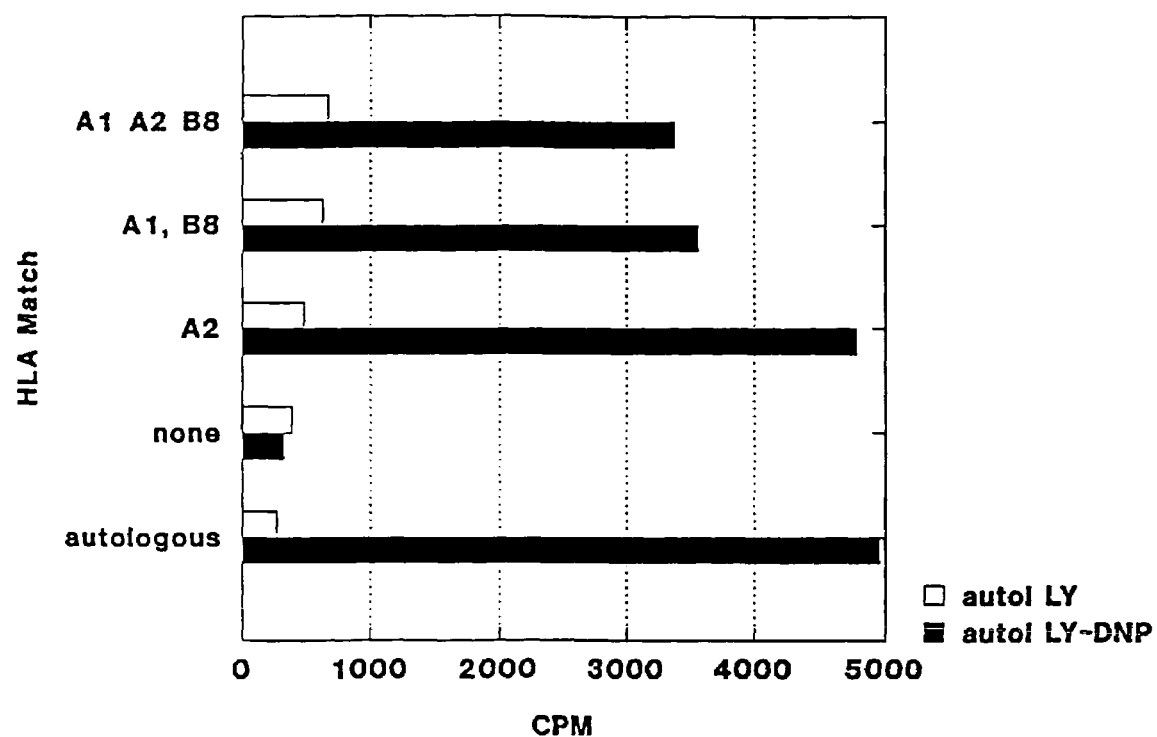
FIG. 10 exhibits MHC restriction of T cell response. Expanded CD8+ T cells (HLA-A1, A2, B8, Bw6) were tested for ability to proliferate in response to DNP-modified autologous PBL and to DNP modified allogeneic PBL from four other patients. Three of the allogeneic stimulators were matched at one or more class I loci as shown, and the fourth was completely mismatched (A24, A26, B44, B63). Cultures were pulsed with $^{125}$IUDR on day 6.

DNP-reactive CD8+ T cells obtained by panning of the bulk population were able to be maintained in long-term (>3 months) culture in IL2-containing medium by repeated stimulation with DNP-modified autologous B lymphoblastoid cells; they retained the stable phenotype, CD3+, CD8+. Two lines of evidence confirmed that their response was MHC class I restricted: 1) Gamma interferon production was blocked by pre-incubation of stimulator cells with anti-class I framework antibody, but not by anti-class II antibody (FIG. 9), 2) The T cells were able to respond to allogeneic DNP-modified stimulators that were matched at one or both HLA-A loci, but not to stimulators that were HLA-A mismatched. As shown in FIG. 10, T cells proliferated upon stimulation with DNP-modified autologous PBL (HLA-A1, A2, B8+, Bw6) and with DNP-modified allogeneic PBL that expressed A1 or A2 or both; no response was elicited by DNP-modified allogeneic stimulators that were A1 and A2-negative.

Cytotoxicity—Melanoma targets were labeled for two hours with $^{51}$Cr (Amersham Corp, Arlington Heights, Ill.), and 2500 cells were added to round-bottom microtiter wells. Then effector cells were added to achieve a series of E:T ratios. After 6 hours incubation at 37° C. supernatants were removed and counted in a gamma counter. Lysis was defined as: $([CPM_{test}-CPM_{spontaneous}]/[CPM_{total}-CPM_{spontaneous}])$ *100.

Figure 11A:
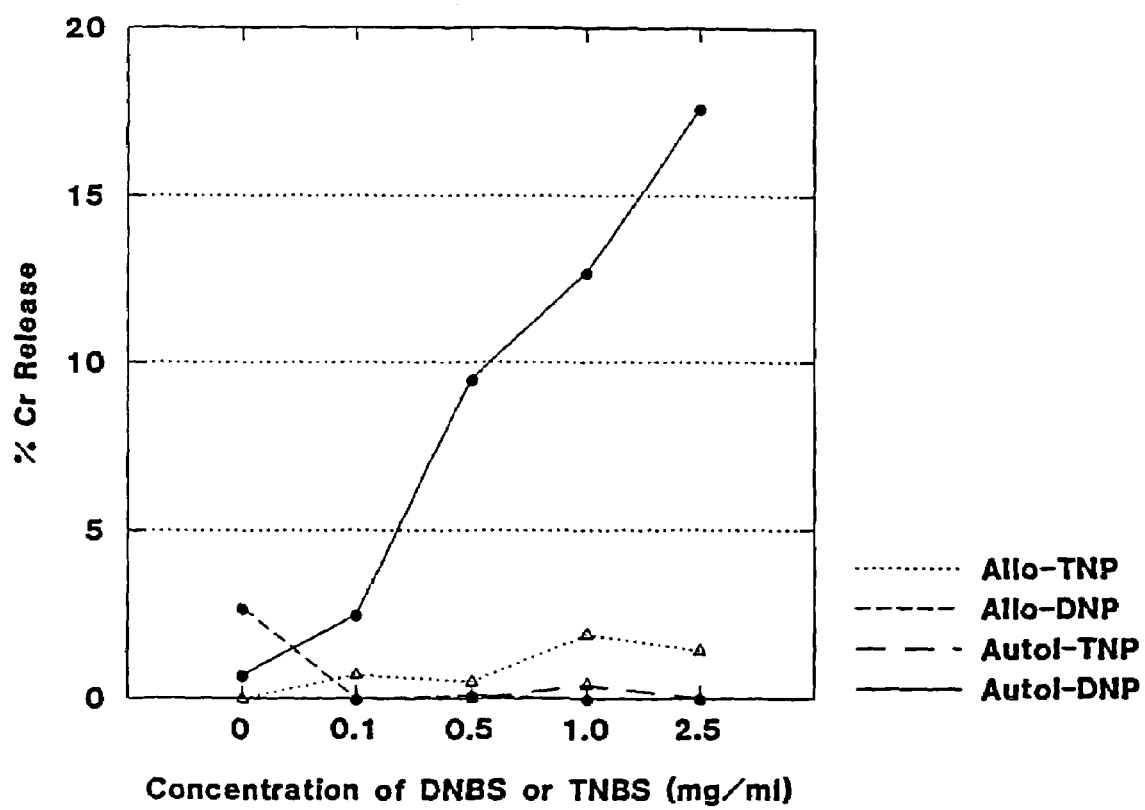
FIG. 11A—target cells were haptenized with various concentrations of DNBS or TNBS. The effector: target cell ratio was 20:1.
Figure 11B:
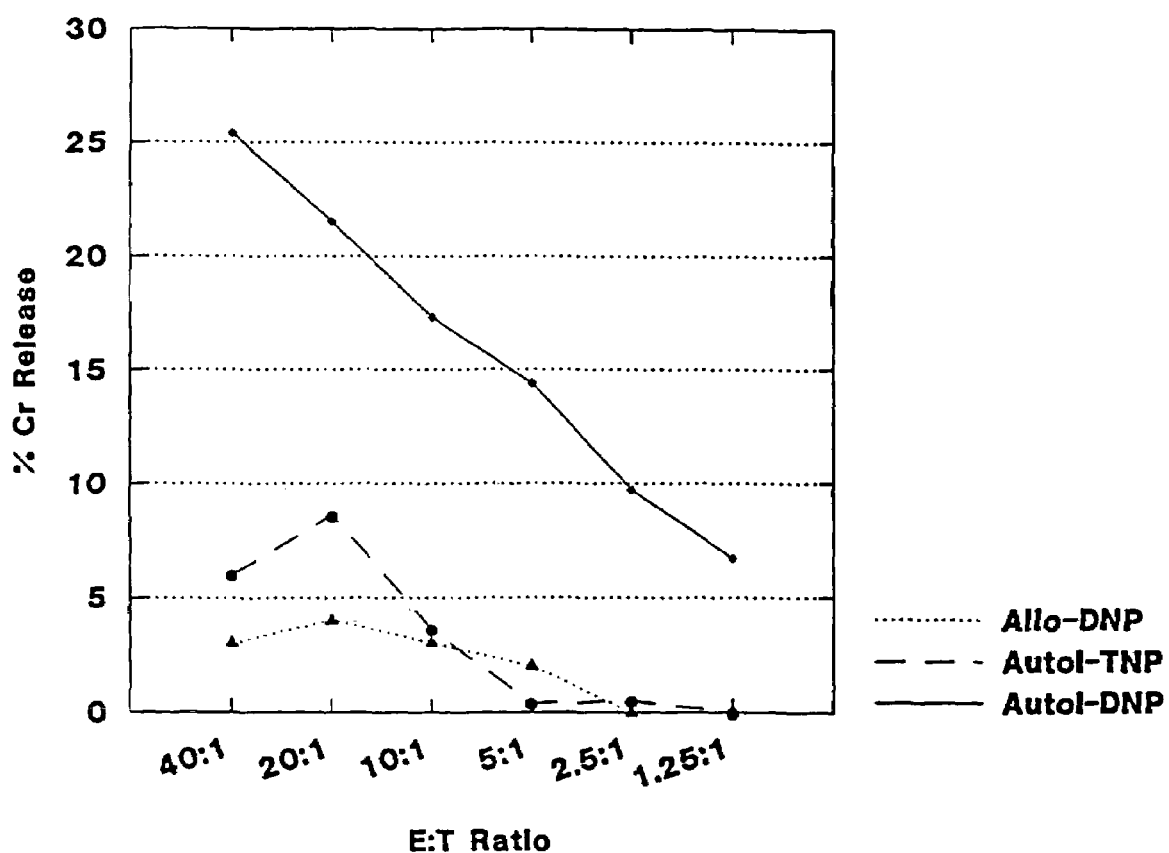
FIG. 11B—Target cells haptenized with 2.5 mg/ml DNBS or TNBS were mixed with effector cells at a series of effector: target (E:T) ratios.

The cytotoxicity of the CD8+ T cell line was tested in a $^{51}$Cr-release assay with autologous melanoma cells as targets. To minimize spontaneous Cr release, DNP modification was accomplished with DNBS rather than DNFB. T cells lysed DNP-modified autologous melanoma cells but not allogeneic (class I-mismatched) melanoma cells (FIGS. 11a, 11b). There was a direct relationship between susceptibility to lysis and the degree of DNP modification, as determined by the concentration of DNBS used. Neither autologous nor allogeneic targets modified with TNP were lysed.

Example 6

Clinical data was collected to suggest that an autologous, DNP-conjugated melanoma vaccine prolongs disease-free survival (DFS) and total survival (TS) in melanoma patients with bulky but resectable regional lymph node metastases. Forty-seven patients underwent standard lymphadenectomy with resection of metastatic masses. Tumor cells were enzymatically-dissociated from these tissues and cryopreserved. Vaccines consisted of $10\times10^6$ to $20\times10^6$ irradiated (2500 cGy) melanoma cells, conjugated to DNP and mixed with BCG. They were injected i.d. every 28 days for a total of 8 treatments. Cyclophosphamide 300 mg/M$^2$ i.v. was given 3 days before the first 2 vaccines only. The DFS and TS of these patients were compared with those of 22 melanoma patients with resected nodal metastases treated previously with an unconjugated vaccine, see Example 4. Of 36 patients with stage 3 melanoma (palpable mass in one lymph node region), 22 are disease-free with a median follow-up of 33 months. Kaplan-Meir analysis projects a 3 year disease-free survival (DFS) and total survival of 59% and 71%, respectively. In contrast, the DFS and TS of stage 3 patients treated with unconjugated vaccine was 22% and 27% respectively (p=0.01, log-rank test). Of 11 stage 4 patients (palpable mass in two lymph node regions), 5 are NED (no evidence of disease) with a median follow-up of 41 months. For both stage 3 and 4 patients, the highest rate of relapse was in the first 6 months, a time when anti-melanoma immunity might not have yet been established. This experiment will be followed by an accelerated schedule of immunizations to reduce the rate of early relapses and improve the overall clinical outcome. The patients were compared to their condition prior to treatment with the vaccine. The patients treated prior to the vaccine study were removed from treatment one to two months prior to starting the vaccine study. Accordingly, the patients were untreated beginning the vaccine study.

Example 7

Clinical and preclinical studies have demonstrated that the development of cellular versus humoral immune responses is directed by the activity of TH1 and TH2 helper T cells, respectively and regulated by localized cytokine production. Interferon gamma (IFNγ), associated with TH1 cells, potentiates cell-mediated immunity (T lymphocytes which kill or inactivate tumor cells) while the TH2-associated cytokines, IL4 and IL10, suppress it.

To determine if local cytokine pattern is important in human tumor immunity, melanoma metastases was examined for the presence of mRNA for IFNγ, IL4, and IL10, by using reverse transcription PCR and primers specific for these cytokines. PCR was carried out according to the method of Yamamura et al., *Science*, 1991, 254, 277, the disclosure of which is hereby incorporated by reference in its entirety. Biopsies of metastatic lesions from 9/10 patients showed high levels of mRNA for IL10 and 3/10 for IL4. Melanoma cell lines established from biopsies also had high levels of IL10 mRNA, indicating that the tumor cells constituted one source of IL10 in the tissues. IFNγ mRNA was found in only 2/10 specimens; both of these had developed T cell infiltration after immunotherapy with a dinitrophenyl (DNP)-conjugated melanoma vaccine. These results suggest that IL10 production by melanoma cells may be important in down-regulating T cell-mediated immunity within tumor tissue and that active immunotherapy may reverse the immunosuppression by stimulating in situ production of IFNγ. The patients were compared to their condition prior to treatment with the vaccine. The patients treated prior to the vaccine study were removed from treatment one to two months prior to starting the vaccine study. Accordingly, the patients were untreated beginning the vaccine study.

Various modifications of the invention in addition to those shown and described herein will be apparent to those skilled in the art from the foregoing description. Such modifications are also intended to fall within the scope of the appended claims.

What is claimed is:

1. A method of treating a malignant tumor in a human patient comprising co-administering to the patient
    (a) a composition comprising a therapeutically effective amount of human tumor cells that:
        (i) are conjugated to a hapten;
        (ii) are of the same tumor type as the malignant tumor of said patient for treatment of whom the composition is intended;
        (iii) are autologous to said patient; and
        (iv) have been rendered incapable of growing in the body of a human upon injection therein; and
    (b) an adjuvant;
    wherein said malignant tumor is from a cancer selected from the group consisting of melanoma cancer, lung cancer, colon cancer, breast cancer, kidney cancer, and prostate cancer; and
    wherein said administration elicits a delayed-type hypersensitivity response by said patient to tumor cells conjugated to said hapten; and
    repeating said administration.

2. The method of claim 1, wherein said hapten is selected from the group consisting of dinitrophenyl, trinitrophenyl, and N-iodoacetyl-N'-(5-sulfonic 1-naphtyl)ethylene diamine.

3. The method of claim 1 wherein said hapten is dinitrophenyl.

4. The method of claim 1, further comprising administering a therapeutically effective amount of cyclophosphamide prior to the first administration of said composition.

5. The method of claim 4 further comprising sensitizing the patient with a therapeutically effective amount of 1-fluoro-2, 4-dinitrobenzene prior to administering the thereapeutically effective amount of cyclophosphamide.

6. The method of claim 1 wherein said adjuvant is Bacillus Calmette-Guerin.

7. The method of claim 1 wherein said administration of said composition prolongs survival of said patient.

8. The method of claim 1, wherein said administration of said composition elicits T lymphocytes that infiltrate the tumor of said human.

* * * * *